US007160724B2

(12) United States Patent
Sanberg et al.

(10) Patent No.: US 7,160,724 B2
(45) Date of Patent: Jan. 9, 2007

(54) HUMAN CORD BLOOD AS A SOURCE OF NEURAL TISSUE FOR REPAIR OF THE BRAIN AND SPINAL CORD

(75) Inventors: Paul Sanberg, Spring Hill, FL (US); Juan Sanchez-Ramos, Tampa, FL (US); Alison Willing, Tampa, FL (US); Daniel D. Richard, Sedona, AZ (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/801,221

(22) Filed: Mar. 7, 2001

(65) Prior Publication Data
US 2002/0028510 A1    Mar. 7, 2002

Related U.S. Application Data

(60) Provisional application No. 60/269,238, filed on Feb. 16, 2001, provisional application No. 60/188,069, filed on Mar. 9, 2000.

(51) Int. Cl.
*C12N 5/00* (2006.01)
*C12N 5/02* (2006.01)
*C12N 5/08* (2006.01)

(52) U.S. Cl. ............... 435/377; 435/325; 435/366; 435/368; 435/372

(58) Field of Classification Search ........ 435/325, 435/352, 354, 360, 366, 368, 377, 383, 384, 435/385, 386, 387, 375, 455, 372; 424/93.1, 424/93.7
See application file for complete search history.

(56) References Cited

U.S. PATENT DOCUMENTS

| 5,690,927 | A | 11/1997 | Major et al. |
| 5,753,491 | A | 5/1998 | Major et al. |
| 5,869,463 | A | 2/1999 | Major et al. |
| 2002/0110546 | A1 | 8/2002 | Major et al. |
| 2002/0146821 | A1 | 10/2002 | Sanchez-Ramos et al. |
| 2003/0039639 | A1 | 2/2003 | Prockop et al. |

FOREIGN PATENT DOCUMENTS

| WO | WO 99/43286 | 9/1999 |
| WO | WO 99/56759 | 11/1999 |

OTHER PUBLICATIONS

Jackowski, AJ (1995) Neural injury repair: hope for the future as barriers to effective CNS regeneration become clearer. British J. of Neurosurgery 9: 303-317.*
Kopen et al. (1999) Marrow stromal cells migrate through the forebrain and cerebellum, and they differentiate into astrocytes after injection into neonatal mouse brains.*
Reynolds et al. (1992) Generation of neurons and astrocytes from isolated cells of the adult mammalian central nervous system. Science 255: 1707-1710.*
Azizi et al. Engraftment and migration of human bone marrow stromal cells implanted in the brains of albino rats—similarities to astrocyte grafts. Proc. Natl. Acad. Sci. USA 95: 3908-3913.*
Dunbar et al. (1994) Gene transfer into hematopoietic progenitor and stem cells: Progress and problems. Stem Cells 12: 563-576.*
Bonnet, D. (2002) Haematopoietic stem cells. Journal of Pathology 197: 430-440.*
Filbin, M.T. (2003) Myelin-associated inhibitors of axonal regeneration in the adult mammalian CNS. Nature Reviews Neuroscience 4: 1-11.*
Grados-Munro et al. (2003) Myelin-associated inhibitors of axon regeneration. Journal of Neuroscience Research 74: 479-485.*
Mehler et al. (1999) Progenitor cell biology: Implications for neural regeneration. Archives of Neurology 56: 780-784.*
Hematological Oncology, 17:1-10, 1999, Simone, Santis, Vigenti, Papa, Amadori, Aloe © 1999 by John Wiley & Son, Ltd.
Nature Neuroscience, vol. 2, No. 4, Apr. 1999, Jonathan Corcoran, Malcolm Maden © Jan. 27, 1999 by Nature America Inc., Received Nov. 8, 1998.
Cell Transplantation, vol. 5, No. 2, 131-143, 1996, Dinsmore, Ratliff, Deacon, Pakzaban, Jacoby, Galpern, Isacson © 1996 by Elsevier Science Inc., Received Oct. 13, 1995.
Mechanisms of Development, 53: 275-287, 1995, Strübing, Ahnert-Hilger, Shan, Wiedenmann, Hescheler, Wobus © 1995 by Elsevier Science Ireland Ltd., Received Jun. 9, 1995, Revision received Aug. 4, 1995.
Stroke, vol. 32, pp. 2682-2688, 2001, Chen et al. © 2001 by American Heart Association, Inc.
Experimental Neurology, vol. 171, pp. 109-115, 2001, Sanchez-Ramos, Song, Kamath, Zigova, Willing, Cardozo-Pelaez, Stedeford, Chopp, Sanberg © 2001.
Flax J. E., et al., (1998) "Engraftable Human Neural Stem Cells Respond to Developmental Cues, Replace Neurons, and Express Foreign Genes," *Nature Biotechnology, Nature America*, Inc. 16:1033-1039.
Hurlbert, M.S., et al., (1999) "Neural Transplantation of hNT Neurons for Huntington's Disease," *Cell Transplantation*, 8:143-151.
Lu L., et al., (1996) "Stem Cells from Bone Marrow, Umbilical Cord Blood and Peripheral Blood for Clinical Application: Current Status and Future Application," *Critical Reviews in Oncology/Hematology*. 22:61-78.
McKay R., (1997) "Stem Cells in the Central Nervous System," *Science*, 276:66-71.
Sirchia G., et al., (1999) "Placenta/Umbilical Cord Blood Transplantation," *Haematologica*, 84:738-747.

* cited by examiner

*Primary Examiner*—Anne-Marie Falk
(74) *Attorney, Agent, or Firm*—Barbara J. Luther; The Luther Law Firm

(57) ABSTRACT

The present invention relates to the use of umbilical cord blood cells from a donor or patient to provide neural cells which may be used in transplantation. The isolated cells according to the present invention may be used to effect autologous and allogeneic transplantation and repair of neural tissue, in particular, tissue of the brain and spinal cord and to treat neurodegenerative diseases of the brain and spinal cord.

2 Claims, 9 Drawing Sheets

HUMAN CORD BLOOD AS A SOURCE OF NEURAL TISSUE FOR REPAIR OF THE BRAIN AND SPINAL CORD

RELATED APPLICATIONS

This application derives priority from provisional application No. 60/188,069, filed Mar. 9, 2000 and 60/269,238, filed Feb. 16, 2001, of the same title.

FIELD OF THE INVENTION

The present invention relates to the use of human umbilical cord blood and/or mononuclear cell fragment, thereof from a donor or patient to provide neural cells for use in transplantation. The isolated cells according to the present invention may be used to effect transplantation and repair of neural tissue, in particular, tissue of the brain and spinal cord and to treat neurodegenerative diseases and injury of the brain and spinal cord.

BACKGROUND OF THE INVENTION

Neurobiologists believe that the neurons in the adult brain and spinal cord are impossible to rebuild once they are damaged. Thus, science provided little hope to patients suffering from brain and spinal cord injury or from neurodegenerative diseases such as Alzheimer's disease and Parkinson's disease, among a number of others. Parkinson's and Alzheimer's diseases are examples of neurodegenerative diseases which are thought to be untreatable.

Parkinson's disease (PD), is a disorder of middle or late life, with very gradual progression and a prolonged course. HARRISON'S PRINCIPLES OF INTERNAL MEDICINE, Vol. 2, 23d ed., Ed by Isselbacher, Braunwald, Wilson, Martin, Fauci and Kasper, McGraw-Hill Inc., New York City, 1994, pg. 2275. The most regularly observed changes in patients with Parkinson's disease have been in the aggregates of melanin-containing nerve cells in the brainstem (substantia nigra, locus 20 coeruleus), where there are varying degrees of nerve cell loss with reactive gliosis (most pronounced in the substantia nigra) along with distinctive eosinophilic intracytoplasmic inclusions. (Id. at 2276). In its fully developed form, PD is easily recognized in patients, where stooped posture, stiffness and slowness of movement, fixity of facial expression, rhythmic tremor of the limbs, which subsides on active willed movement or complete relaxation, are common features. Generally, accompanying the other characteristics of the fully developed disorder is the festinating gait, whereby the patient, progresses or walks with quick shuffling steps at an accelerating pace as if to catch up with the body's center of gravity. (Id. at 2276).

The treatment of Parkinson's disease pharmacologically with levodopa combined with stereotactic surgery has only represented a partial cure, at best. (Id. at 2277). Underlying much of the treatment difficulty is directed to the fact that none of these therapeutic measures has an effect on the underlying disease process, which consists of neuronal degeneration. Ultimately, a point seems to be reached where pharmacology can no longer compensate for the loss of basal ganglia dopamine. (Id.).

Alzheimer's Disease (AD) is caused by a degenerative process in the patient which is characterized by progressive loss of cells from the basal forebrain, cerebral cortex and other brain areas. Acetylcholine transmitting neurons and their target nerves are particularly affected. Senile plaques and neurofibrillary tangles are present. Pick's disease has a similar clinical picture to Alzheimer's disease but a somewhat slower clinical course and circumscribed atrophy, mainly affecting the frontal and temporal lobes. One animal model for Alzheimer's disease and other dementias displays hereditary tendency toward the formation of such plaques. It is thought that if a drug has an effect in the model, it also may be beneficial in at least some forms of Alzheimer's and Pick's diseases. At present there are palliative treatments but no means to restore function in Alzheimer's patients.

A group of related neuronal degenerative disorders is characterized by progressive ataxia due to degeneration of the cerebellum, brainstem, spinal cord and peripheral nerves, and occasionally the basal ganglia. Many of these syndromes are hereditary; others occur sporadically. The spinocerebellar degenerations are logically placed in three groups: predominantly spinal ataxias, cerebellar ataxias and multiple-system degenerations. To date there are no treatments. Friedrich's ataxia is the prototypical spinal ataxia whose inheritance is autosomal recessive. The responsible gene has been found on Chromosome 9. Symptoms begin between ages of 5 and 15 with unsteady gait, followed by upper extremity ataxia and dysarthria. Patients are flexic and lose large-fiber sensory modalities (vibration and position sense). Two other diseases have similar symptoms: Bassen-Kornzweig syndrome (abeta-lipoproteinemia and vitamin E deficiency) and Refsom's disease (phytanic acid storage disease). Cerebellar cortical degenerations generally occur between ages 30 and 50. Clinically only signs of cerebellar dysfunction can be detected, with pathologic changes restricted to the cerebellum and occasionally the inferior olives. Inherited and sporadic cases have been reported. Similar degeneration may also be associated with chronic alcoholism. In multiple-system degenerations, ataxia occurs in young to middle adult life in varying combinations with spasticity and extrapyramidal, sensory, lower motor neuron and autonomic dysfunction. In some families, there may also be optic atrophy, retinitis pigmentosa, ophthalmoplegia and dementia.

Another form of cerebellar degeneration is paraneoplastic cerebellar degeneration that occurs with certain cancers, such as oat cell lung cancer, breast cancer and ovarian cancer. In some cases, the ataxia may precede the discovery of the cancer by weeks to years. Purkinje cells are permanently lost, resulting in ataxia. Even if the patient is permanently cured of the cancer, their ability to function may be profoundly disabled by the loss of Purkinje cells. There is no specific treatment.

Strokes also result in neuronal degeneration and loss of functional synapses. Currently there is no repair, and only palliation and rehabilitation are undertaken.

Neurotransplantation has been used to explore the development of the central nervous system and for repair of diseased tissue in conditions such as Parkinson's and other neurodegenerative diseases. The experimental replacement of neurons by direct grafting of fetal tissue into the brain has been accomplished in small numbers of patients in several research universities (including the University of South Florida); but so far, the experimental grafting of human fetal neurons has been limited by scarcity of appropriate tissue sources, logistic problems, legal and ethical constraints, and poor survival of grafted neurons in the human host brain. One method replaces neurons by using bone marrow stromal cells as stem cells for non-hematopoietic tissues. Marrow stromal cells can be isolated from other cells in marrow by their tendency to adhere to tissue culture plastic. The cells have many of the characteristics of stem cells for tissues that can roughly be defined: as mesenchyrnal, because they can be differentiated in culture into osteoblasts, chondrocytes, adipocytes, and even myoblasts. This population of bone marrow cells (BMSC) have also been used to prepare dendritic cells, (K. Inaba, et al., *J Experimental Med.* 176: 1693–1702 (1992)) which, as the name implies, have a morphology which might be confused for neurons. Dendritic cells comprise a system of antigen-presenting cells involved in the initiation of T cell responses. The specific growth factor, which stimulates production of dendritic cells, has been reported to be granulocyte/macrophage colony-stimulating factor 30 (GM-CSF). K. Inaba, et al., *J Experimental Med.* 176: 1693–1702 (1992).

Work has recently been performed using stem cells obtained from bone marrow to provide neural cells which can be used in neuronal transplantation. See WO 99/56759. This patent represented the culmination of more than 130 years of work in the use of bone marrow stem cells for non-hematopoietic uses.

Several groups of investigators since 1990 have attempted to prepare more homogenous populations of stem cells from bone marrow. For example, U.S. Pat. No. 5,087,570, issued Feb. 11, 1992, discloses how to isolate homogeneous mammalian hematopoietic stem cell compositions. Concentrated hematopoietic stem cell compositions are substantially free of differentiated or dedicated hematopoietic cells. The desired cells are obtained by subtraction of other cells having particular markers. The resulting composition may be used to provide for individual or groups of hematopoietic lineages, to reconstitute stem cells of the host, and to identify an assay for a wide variety of hernatopoietic growth factors.

U.S. Pat. No. 5,633,426 issued May 27, 1997, is another example of the differentiation and production of hematopoietic cells. Chimeric immunocompromised mice are given human bone marrow of at least 4 weeks from the time of implantation. The bone marrow assumed the normal population of bone marrow except for erythrocytes. These mice with human bone marrow may be used to study the effect of various agents on the proliferation and differentiation of human hematopoietic cells.

U.S. Pat. No. 5,665,557, issued Sep. 9, 1997, relates to methods of obtaining concentrated hematopoietic stem cells by separating out an enriched fraction of cells expressing the marker CDw 109. Methods of obtaining compositions enriched in hematopoietic megakaryocyte progenitor cells are also provided. Compositions enriched for stem cells and populations of cells obtained therefrom are also provided by the invention. Methods of use of the cells are also included.

U.S. Pat. No. 5,453,505 issued on Jun. 5, 1995, is yet another method of differentiation. Primordial tissue is introduced into immunodeficient hosts, where the primordial tissue develops and differentiates. The chimeric host allows for investigation of the processes and development of the xenogeneic tissue, testing for the effects of various agents on the growth and differentiation of the tissue, as well as identification of agents involved with the growth and differentiation.

U.S. Pat. No. 5,753,505 issued May 19, 1998, provides an isolated cellular composition comprising greater than about 90% mammalian, non-tumor-derived, neuronal progenitor cells which express a neuron-specific marker and which can give rise to progeny which can differentiate into neuronal cells. Also provided are methods of treating neuronal disorders utilizing this cellular composition.

U.S. Pat. No. 5,759,793 issued Aug. 6, 1996, provides a method for both the positive and negative selection of at least one mammalian cell population from a mixture of cell populations utilizing a magnetically stabilized fluidized bed. One application of this method is the separation and purification of hematopoietic cells. Target cell populations include human stem cells.

U.S. Pat. No. 5,789,148 issued Aug. 4, 1998, discloses a kit, composition and method for cell separation. The kit includes a centrifugable container and an organosilanized silica particle-based cell separation suspension suitable for density gradient separation, containing a polylactam and sterilized by treatment with ionizing radiation. The composition includes a silanized silica particle-based suspension for cell separation which contains at least 0.05% of a polylactam, and preferably treated by ionizing radiation. Also disclosed is a method of isolating rare blood cells from a blood cell mixture.

Within the past several years, mesenchymal stem cells (MSCs) have been explored as vehicles for both cell therapy and gene therapy. The cells are relatively easy to isolate from the small aspirates of bone marrow that can be obtained under local anesthesia: they are also relatively easy to expand in culture and to transfect with exogenous genes. Prockop, D. J. Science 26: 71–74 (1997). Therefore, MSCs appear to have several advantages over hematopoietic stem cells (HMCs) for use in gene therapy. The isolation of adequate numbers of HSCs requires large volumes of marrow (I liter or more), and the cells are difficult to expand in culture. (Prockop, io D. J. (ibid.)).

There are several sources for bone marrow tissue, including the patient's own bone marrow, that of blood relatives or others with MHC matches and bone marrow banks. There are several patents that encompass this source. U.S. Pat. No. 5,476,997 issued May 17, 1994, discloses a method of producing human bone marrow equivalent. A human hematopoietic system is provided in an immunocompromised mammalian host, where the hematopoietic system is functional for extended periods of time. In this method, human fetal liver tissue and human fetal thymus are introduced into a young immunocompromised mouse at a site supplied with a vascular system, whereby the fetal tissue results in formation of functional human bone marrow tissue.

Human fetal tissue also represents a source of implantable neurons, but its use is quite controversial. U.S. Pat. No. 5,690,927 issued Nov. 25, 1997, also utilizes human fetal tissue. Human fetal neuro-derived cell lines are implanted into host tissues. The methods allow for treatment of a variety of neurological disorders and other diseases.

U.S. Pat. No. 5,753,491, issued May 19, 1998, discloses methods for treating a host by implanting genetically unrelated cells in the host. More particularly, the present invention provides human fetal neuro-derived cell lines, and methods of treating a host by implantation of these immortalized human fetal neuro-derived cells into the host. One source is the mouse, which is included in the U.S. Pat. No. 5,580,777 issued Dec. 3, 1996. This patent features a method for the in vitro production of lines of immortalized neural precursor cells, including cell lines having neuronal and/or glial cell characteristics, comprises the step of infecting neuroepithelium or neural crest cells with a retroviral vector carrying a member of the myc family of oncogenes.

U.S. Pat. No. 5,753,506 issued May 19, 1998, reveals an in vitro procedure by which a homogeneous population of multipotential precursor cells from mammalian embryonic neuroepithelium (CNS stem cells) is expanded up to 10 fold in culture while maintaining their multipotential capacity to differentiate into neurons, oligodendrocytes, and astrocytes. Chemical conditions are presented for expanding a large number of neurons from the stem cells. In addition, four factors-PDGF, CNTF, LIF, and T3-have been identified which, individually, generate significantly higher proportions of neurons, astrocytes, or oligodendrocytes. These procedures are intended to permit a large-scale preparation of the mammalian CNS stem cells, neurons, astrocytes, and oligodendrocytes. These cells are proposed as an important tool for many cell- and gene-based therapies for neurological disorders. Another source of stem cells is that of primate embryonic stem cells. U.S. Pat. No. 5,843,780 issued Dec. 1, 1998, utilizes these stem cells. A purified preparation of stem cells is disclosed. This preparation is characterized by the following cell surface markers: SSEA-I (−); SSEA-3 (+); TRA-1-60 (+); TRA-1-81 (+); and alkaline phosphatase (+). In one embodiment, the cells of the preparation have normal karyotypes and continue to proliferate in an undifferentiated state after continuous culture for eleven months. The embryonic stem cells lines are also described as retaining the ability to form trophoblasts and to differentiate into tissues derived from all three embryonic germ layers (endoderm, mesoderm and ectoderm). A method for isolating a primate embryonic stem cell line is also disclosed in the patent.

There is substantial evidence in both animal models and human patients that neural transplantation is a scientifically feasible and clinically promising approach to the treatment of neurodegenerative diseases and stroke as well as for repair of traumatic injuries to brain and spinal cord. Nevertheless, alternative cell sources and novel strategies for differentiation are needed to circumvent the numerous ethical and technical constraints that now limit the widespread use of neural transplantation. In short, there is a need for further development of readily available reliable sources of neural cells for transplantation.

The use of umbilical cord blood for use in hematopoietic reconsitution has been around since the work of Ende in the early 1970's. Because umbilical cord blood is rich in hematopoietic precursors, including stem cells, it represents a good source of cells for hematopoietic reconstitution. To date, however, little work has been done on using pluripotential stem cells or related neural precursors which are found in umbilical cord blood for neuronal transplantion perhaps because of the failure to realize the viable source of neuronal precursors which can be found in umbilical cord blood.

Human cord and placental blood provides a rich source of hematopoietic stem cells. On the basis of this finding, umbilical cord blood stem cells have been used to reconstitute hematopoiesis in children with malignant and nonmalignant diseases after treatment with myeloablative doses of chemoradiotherapy. Sirchia and Rebulla, 1999 *Haematologica* 84:738–47. Early results show that a single cord blood sample provides enough hematopoietic stem cells to provide short- and long-term engraftment, and that the incidence and severity of graft-versus-host disease has been low even in HLA-mismatched transplants. These results, together with our previous discovery that bone marrow cells contain stem cells capable of differentiating into neurons and glia, led to the present invention which uses cord blood or mononuclear cell fractions thereof to repair neuronal damage in brain and spinal cord. Sanchez-Ramos, et al. 1998. *Movement Disorders* 13(s2): 122 and Sanchez-Ramos, et al., (2000) *Exp. Neurol*.

OBJECTS OF THE INVENTION

It is an object of the present invention to provide a novel source of pluripotent stem and/or progenitor cells which can be readily differentiated into neuronal and glial cells to be used in transplantation in the brain and spinal cord of a patient and for the treatment of neurodegenerative diseases.

It is an additional object of the invention to provide pharmaceutical compositions comprising effective amounts or concentrations of neural cells for use in transmplantation and methods for treating neurodegenerative diseases, or brain or spinal cord injuries or damage.

It is another object of the invention to provide methods for isolating and inducing differentiation of pluripotent stem and/or progenitor cells into neuronal and glial cells which can be used in tranplantation procedures or for the treatment of neurodegenerative diseases.

It is a further object to provide a method of treating neurodegenerative diseases and spinal cord/brain injury using neural and/or neuronal and/or glial cells derived from umbilical cord blood.

It is yet a further object of the invention to provide a method of transplanting neural and/or neuronal and/or glial cells derived from umbilical cord blood in order to repair damaged organs of a patient's nervous system such as the brain and spinal cord.

These and/or other objects of the invention may be readily gleaned from the description of the invention which follows.

BRIEF DESCRIPTION OF THE INVENTION

The present invention relates to the unexpected discovery that fresh or reconstituted umbilical cord blood or a mononuclear cellular fraction thereof is a novel source of cells which can be differentiated into neural cells and/or neuronal tissue and used for neuronal transplantation (autografting as well as allografting), thus obviating the need to use pooled neuronal fetal tissue or bone marrow tissue, which is often hard to obtain. Thus, the present invention may be used for autografting (cells from an individual are used in that same individual), allografting (cells from one person are used in another person) and xenografting (transplantation from one species to another). In this aspect of the present invention, it has unexpectedly been discovered that umbilical cord blood from neonates or fetuses comprises cells which may be induced to become neurons in vitro and in vivo. These cells may be used in autologous or allogeneic transplantation (grafting) procedures to improve neurological deficit and to effect transplantation and repair of neural/neuronal tissue, in particular, tissue of the brain and spinal cord and to treat neurodegenerative diseases of the brain and spinal cord.

In one aspect according to the present invention, umbilical cord blood derived neural cells are suitable for grafting into a patient's brain or spinal cord. These neural cells may be purified and/or incubated with a differentiation agent by any one or more of the methods otherwise described in the present specification or alternatively, these cells may be obtained from crude mononuclear cell fractions of umbilical cord blood and used directly without further purification or differentiation. In other aspects, umbilical cord blood may be used without further purification.

In another aspect of the present invention, there is presented a method for obtaining neural cells from umbilical cord blood, the method comprising the steps of obtaining umbilical cord blood, selecting umbilical cord pluripotential stem cells or progenitor cells which are neural precursor cells and incubating the umbilical cord stem cells or progenitor cells with a differentiation agent to change the phenotype of the cells to produce a population of neural cells which are capable of being transplanted. The steps of the method may also be changed such that all of the cells (for example, from an umbilical blood sample or a mononuclear cell fraction thereof) are incubated with a differentiation agent prior to separation of the neural phenotype cells.

The method of the present invention may include the step of separating the pluripotential stem and progenitor cells from a population of mononuclear cells obtained from umbilical cord blood using a magnetic cell separator to separate out all cells which contain a CD marker, and then expanding the cells which do not contain a marker in a growth medium containing a differentiation agent such as retinoic acid, fetal neuronal cells or a growth factor such as BDNF, GDNF and NGF or mixtures, thereof, among numerous others. Preferably, a mixture of retinoic acid and at least one growth factor, for example, nerve growth factor, is used as the differentiation agent. The retinoic acid may be 9-cis retinoic acid, all-transretinoic acid and mixtures thereof. The separation and incubation (differentiation) steps, may be interchanged.

Alternatively, an enriched cell population of pluripotent stem and/or progenitor cells may be obtained from a population of mononuclear cells obtained from umbilical cord blood by subjecting the mononuclear population to an amount of an anti-proliferative agent (such as Ara-C [cytidine arabinoside] or methotrexate, among others) effective to eliminate all or substantially all proliferating cells and then exposing the remaining non-proliferating cells to a mitogen such as epidermal growth factor or other mitogen (including other growth factors) to provide a population of differentiated cells and quiescent cells (pluripotent stem or progenitor cells) which population is grown in culture medium such that the quiescent cells are concentrated in the cell population to greatly outnumber the differentiated cells. The pluripotent stem and/or progenitor cells obtained may then be grown in a cell medium containing a differentiation agent as generally described above in order to change the phenotype of the stem and/or progenitor cells to neuronal and/or glial cells which cells may be used in transplantation procedures directly without further purification.

The umbilical cord blood sample from which the pluripotent stem and/or progenitor cells are obtained may be fresh umbilical cord blood, reconstituted cryopreserved umbilical cord blood or a fresh or reconstituted cryopreserved mononuclear fraction thereof.

Novel compositions according to the present invention comprise umbilical cord blood or a mononuclear cellular fraction thereof, in combination with an effective amount of at least one neural cell differentiation agent. Neural cell differentiation agents for use in the present invention include for example, retinoic acid, fetal or mature neuronal cells including mesencephalic or striatal cells or a growth factor or cytokine such as brain derived neurotrophic factor (BDNF), glial derived neurotrophic factor (GDNF), glial growth factor (GFF) and nerve growth factor (NGF) or mixtures, thereof. Additional differentiation agents include, for example, growth factors such as fibroblast growth factor (FGF), transforming growth factors (TGF), ciliary neurotrophic factor (CNTF), bone-morphogenetic proteins (BMP), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, thrombopoietin, silencers, (including glial-cell missing, neuron restrictive silencer factor), antioxidants such as vitamin E (tocopherol) and vitamin E esters, among others including lipoic acid, SHC (SRC-homology-2-domain-containing transforming protein), neuroproteins, proteoglycans, glycoproteins, neural adhesion molecules, and other cell-signalling molecules and mixtures, thereof.

Also presented is a cell line of pluripotent stem and/or progenitor cells produced by any one or more of the above-described methods such that the cells have the ability to migrate and localize to specific neuroanatomical regions where they differentiate into neuronal or glial cells typical of the region at the cite of transplantation and integrate into the tissue in a characteristic tissue pattern. Pharmaceutical compositions utilizing these cells or other neural cells are also an aspect of the present invention.

The present invention also is directed to a kit for neuronal transplantation comprising a flask with dehydrated culture medium and a pluripotent stem and/or progenitor cells and/or other neural cells.

The present invention is also directed to a method for treating a neurodegenerative disorder or a brain or spinal cord injury or neurological deficit comprising administering to (preferably, transplanting in) a patient suffering from such injury, a neurodegenerative disorder or neurlogical deficit an effective amount of neural and/or neuronal and/or glial cells according to the present invention. Neurodegenerative disorders which can be treated using the method according to the present invention include, for example, Parkinson's disease, Huntington's disease, multiple sclerosis (MS), Alzheimer's disease, Tay Sach's disease (beta hexosaminidase deficiency), lysosomal storage disease, brain and/or spinal cord injury occurring due to ischemia, spinal cord and brain damage/injury, ataxia and alcoholism, among others, including a number which are otherwise described herein.

The present invention is also directed to a method of treating neurological damage in the brain or spinal cord which occurs as a consequence of genetic defect, physical injury, environmental insult or damage from a stroke, heart attack or cardiovascular disease (most often due to ischemia) in a patient, the method comprising administering (including transplanting), an effective number or amount of neural cells obtained from umbilical cord blood to said patient, including directly into the affected tissue of the patient's brain or spinal cord. Administering cells according to the present invention to a patient and allowing the cells to migrate to the appropriate cite within the central nervous system is another aspect of the present invention.

A method of obtaining neural and/or neuronal and/or glial cells for autologous transplantation from an individual's own umbilical cord blood comprises the steps of 1) harvesting mononuclear cells from fresh or cryopreserved umbilical cord blood or a cryopreserved mononuclear fraction of umbilical cord blood; 2) separating out the pluripotent stem cells and/or progenitor cells from the cord blood or mononuclear fraction; 3) incubating the stem cells and/or progenitor cells in a medium which includes an effective amount of a mitogen; and 4) incubating the stem and/or progenitor cells obtained from step 3 with a differentiation agent.

DETAILED DESCRIPTION OF THE INVENTION

Figure 1A:
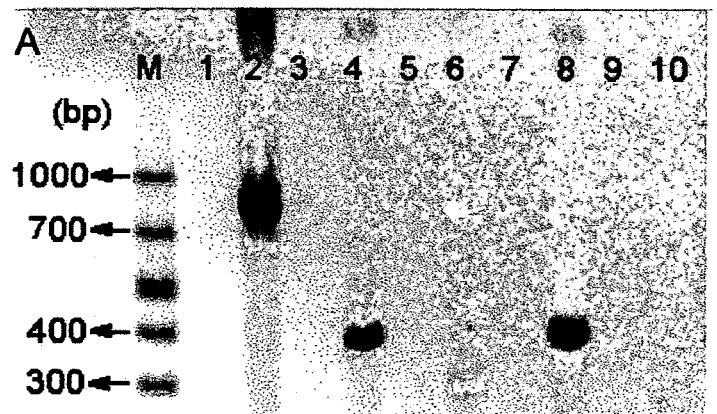
FIG. 1 is representative of results of gel studies indicating the presence of mRNA from neuronal phenotypes.

The following definitions are used throughout the specification to describe the present invention.

The term "patient" is used throughout the specification to describe an animal, preferably a human, to whom treatment, including prophylactic treatment, with the compositions according to the present invention, is provided. For treatment of those infections, conditions or disease states which are specific for a specific animal such as a human patient, the term patient refers to that specific animal. The term "donor" is used to describe an individual (animal, including a human) who or which donates umbilical cord blood for use in a patient.

The term "umbilical cord blood" or "cord blood" is used throughout the specification to refer to blood obtained from a neonate or fetus, most preferably a neonate and preferably refers to blood which is obtained from the umbilical cord or the placenta of newborns. The use of cord or placental blood as a source of mononuclear cells is advantageous because it can be obtained relatively easily and without trauma to the donor. In contrast, the collection of bone marrow cells from a donor is a traumatic experience. Cord blood cells can be used for autologous transplantation or allogenic transplantation, when and if needed. Cord blood is preferably obtained by direct drainage from the cord and/or by needle aspiration from the delivered placenta at the root and at distended veins.

The term "effective amount" is used throughout the specification to describe concentrations or amounts of components such as differentiation agents, mitogens, neural and/or neuronal or glial cells, or other agents which are effective for producing an intended result including differentiating stem and/or progenitor cells into neural, neuronal and/or glial cells, or treating a neurodegenerative disease or other neurological condition including damage to the central nervous system of a patient, such as a stroke, heart attack or accident victim or for effecting a transplantation of those cells within the patient to be treated. Compositions according to the present invention may be used to effect a transplantation of the neural cells within the composition to produce a favorable change in the brain or spinal cord, or in the disease or condition treated, whether that change is an improvement (such as stopping or reversing the degeneration of a disease or condition, reducing a neurological deficit or improving a neurological response) or a complete cure of the disease or condition treated.

The term "neural cells" are cells having at least an indication of neuronal or glial phenotype, such as staining for one or more neuronal or glial markers or which will differentiate into cells exhibiting neuronal or glial markers. Examples of neuronal markers which may be used to identify neuronal cells according to the present invention include, for example, neuron-specific nuclear protein, tyrosine hydroxylase, microtubule associated protein, and calbindin, among others. The term neural cells also includes cells which are neural precursor cells, i.e., stem and/or progenitor cells which will differentiate into or become neural cells or cells which will ultimately exhibit neuronal or glial markers, such term including pluripotent stem and/or progenitor cells which ultimately differentiate into neuronal and/or glial cells. All of the above cells and their progeny are construed as neural cells for the purpose of the present invention. Neural stem cells are cells with the ability to proliferate, exhibit self-maintenance or renewal over the life-time of the organism and to generate clonally related neural progeny. Neural stem cells give rise to neurons, astrocytes and oligodendrocytes during development and can replace a number of neural cells in the adult brain. Neural stem cells are neural cells for purposes of the present invention. The terms "neural cells" and "neuronal cells" are generally used interchangeably in many aspects of the present invention. Preferred neural cells for use in certain aspects according to the present invention include those cells which exhibit one or more of the neural/neuronal phenotypic markers such as Musashi-1, Nestin, NeuN, class III β-tubulin, GFAP, NF-L, NF-M, microtubule associated protein (MAP2), S100, CNPase, glypican (especially glypican 4), neuronal pentraxin II, neuronal PAS 1, neuronal growth associated protein 43, neurite outgrowth extension protein, vimentin, Hu, internexin, O4, myelin basic protein and pleiotrophin, among others.

The term "administration" or "administering" is used throughout the specification to describe the process by which neural cells according to the present invention are delivered to a patient for treatment purposes. Neural cells may be administered a number of ways including parenteral (such term referring to intravenous and intraarterial as well as other appropriate parenteral routes), intrathecal, intraventricular, intraparenchymal (including into the spinal cord, brainstem or motor cortex), intracisternal, intracranial, intrastriatal, and intranigral, among others which term allows neural cells to migrate to the cite where needed. Neural cells may be administered in the form of whole cord blood or a fraction thereof (such term including a mononuclear fraction thereof or a fraction of neural cells, including a high concentration of neural cells). The compositions according to the present invention may be used without treatment with a differentiation agent ("untreated", i.e., without further treatment in order to promote differentiation of cells within the umbilical cord blood sample) or after treatment ("treated") with a differentiation agent or other agent which causes certain pluripotential stem and/or progenitor cells within the cord blood sample to differentiate into cells exhibiting neuronal and/or glial phenotype. Administration will often depend upon the disease or condition treated and may preferably be via a parenteral route, for example, intravenously, by administration into the cerebral spinal fluid or by direct administration into the affected tissue in the brain. For example, in the case of Alzheimer's disease, Huntington's disease and Parkinson's disease, the preferred route of administration will be a transplant directly into the striatum (caudate cutamen) or directly into the substantia nigra (Parkinson's disease). In the case of amyotrophic lateral sclerosis (Lou Gehrig's disease) and multiple sclerosis, the preferred administration is through the cerebrospinal fluid. In the case of lysosomal storage disease, the preferred route of administration is via an intravenous route or through the cerebrospinal fluid. In the case of stroke, the preferred route of administration will depend upon where the stroke is, but will often be directly into the affected tissue (which may be readily determined using MRI or other imaging techniques).

Each of these conditions, however, may be readily treated using other routes of administration including, for example, an intravenous or intraarterial administration of whole umbilical cord blood or a mononuclear cell fraction thereof to treat a condition or disease state. In the case of such treatment, however, and in particular, the treatment of amyotrophic lateral sclerosis (Lou Gehrig's disease), treatment of the patient using parenteral (in particular, intravenous or intraarterial) administration of whole umbilical cord blood or a mononuclear cellular fraction thereof or other routes of administration will be performed preferably in the absence of radiation or other treatment such as chemotherapy (which are often used to eliminate bone marrow cells or other tissue in the patient in order to impair, destroy and replace hematopoietic cells) before, during or after administration of the umbilical cord blood or mononuclear cell fraction, thereof.

The terms "grafting" and "transplanting" and "graft" and "transplantation" are used throughout the specification synonymously to describe the process by which neural and/or neuronal cells according to the present invention are delivered to the site within the nervous system where the cells are intended to exhibit a favorable effect, such as repairing damage to a patient's central nervous system, treating a neurodegenerative disease or treating the effects of nerve damage caused by stroke, cardiovascular disease, a heart attack or physical injury or trauma or genetic damage or environmental insult to the brain and/or spinal cord, caused by, for example, an accident or other activity. Neural cells for use in the present invention may also be delivered in a remote area of the body by any mode of administration as described above, relying on cellular migration to the appropriate area in the central nervous system to effect transplantation.

The term "essentially" is used to describe a population of cells or a method which is at least 95+% effective, more preferably at least about 98% effective and even more preferably at least 99% effective. Thus, a method which "essentially" eliminates a given cell population, eliminates at least about 95+% of the targeted cell population, most preferably at least about 99% of the cell population. Neural cells according to the present invention, in certain preferred embodiments, are essentially free of hematopoietic cells (i.e., the CD34+ cellular component of the mononuclear cell fragment).

The term "non-tumorigenic" refers to the fact that the cells do not give rise to a neoplasm or tumor. Stem and/or progenitor cells for use in the present invention are generally free from neoplasia and cancer.

The term "cell medium" or "cell media" is used to describe a cellular growth medium in which mononuclear cells and/or neural cells are grown. Cellular media are well known in the art and comprise at least a minimum essential medium plus optional agents such as growth factors, glucose, non-essential amino acids, insulin, transferrin and other agents well known in the art. In certain preferred embodiments at least one differentiation agent is added to the cell media in which a mononuclear cell fraction is grown in order to promote differentiation of certain cells within the mononuclear fraction into neural cells.

In a preferred aspect of the present invention, mononuclear cells grown in standard cellular media (preferably, at least a minimum essential medium supplemented with non-essential amino acids, glutamine, mercaptoethanol and fetal bovine serum (FBS)) are grown in a "neural proliferation medium" (i.e., a medium which efficiently grows neural cells) followed by growth in a "differentiation medium", generally, which is similar to the neural proliferation medium with the exception that specific nerve differentiation agents are added to the medium and in certain cases, other growth factors are limited or removed). A particularly preferred neural proliferation medium is a media which contains DMEM/F12 1:1 cell media, supplemented with 0.6% glucose, insulin (25 µg/ml), transferrin (100 µg/ml), progesterone 20 nM, putrescine (60 µM, selenium chloride 30 nM, glutamine 2 mM, sodium bicarbonate 3 mM, HEPES 5 mM, heparin 2 µg/ml and EGF 20 nm/ml, bFGF 20 ng/ml. One of ordinary skill will readily recognize that any number of cellular media may be used to grow mononuclear cell fractions of umbilical cord blood or to provide appropriate neural proliferation media and/or differentiation media.

The term "separation" is used throughout the specification to describe the process by which pluripotent stem and/or progenitor cells are isolated from a mononuclear cell sample or a sample which contains cells other than the desirable stem and/or progenitor cells, for example, umbilical cord blood or other fragment.

The term "mitogen" is used throughout the specification to describe an agent which is added to non-proliferating cells obtained from a mononuclear cell sample in order to produce differentiated cells and quiescent cells (pluripotent stem and/or progenitor cells). A mitogen is a transforming agent which induces mitosis in certain cells other than pluripotent stem and/or progenitor cells obtained from umbilical cord blood. Preferred mitogens for use in the present invention include epidermal growth factor (EGF), among other agents such as the less preferred pokeweed mitogen, which also may be used to induce mitosis. Mitogens are also any one or a combination of a variety of growth factors which have been shown to exert mitogenic actions on neural and mesenchymal precursors. These growth factors are: Epidermal Growth Factor (EGF) family ligands (EGF, Transforming Growth Factor α, amphiregulin, betacellulin, heparin-binding EGF and Heregulin), basic Fibroblastic growth factors (bFGF) and other members of its superfamily (FGF1, FGF4), members of Platelet-Derived Growth Factor family (PDGF AA, AB, BB), Interleukins, and members of the Transforming Growth Factor β superfamily.

The term "antiproliferative agent" is sued throughout the specificaiton to describe an agent which will prevent the proliferation of cells during methods according to the present invention which enrich pluripotent stem and/or progenitor cells. Exemplary antiproliferative agents include, for example, Ara-C, methotrexate and other antiproliferative agents. Preferred antiproliferative agents are those agents which limit or prevent the growth of proliferating cells within an umbilical cord blood sample or mononuclear cell fraction thereof so that quiescent stem and/or progenitor cells may be enriched.

The term "differentiation agent" or "neural differentiation agent" is used throughout the specification to describe agents which may be added to cell culture (which term includes any cell culture medium which may be used to grow neural cells according to the present invention) containing pluripotent stem and/or progenitor cells which will induce the cells to a neuronal or glial phenotype. Preferred differentiation agents for use in the present invention include, for example, antioxidants, including retinoic acid, fetal or mature neuronal cells including mesencephalic or striatal cells or a growth factor or cytokine such as brain derived neurotrophic factor (BDNF), glial derived neurotrophic factor (GDNF) and nerve growth factor (NGF) or mixtures, thereof. Additional differentiation agents include, for example, growth factors such as fibroblast growth factor (FGF), transforming growth factors (TGF), ciliary neurotrophic factor (CNTF), bone-morphogenetic proteins (BMP), leukemia inhbitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, thrombopoietin, silencers, (including glial-cell missing, neuron restrictive silencer factor), SHC (SRC-homology-2-domain-containing transforming protein), neuroproteins, proteoglycans, glycoproteins, neural adhesion molecules, and other cell-signalling molecules and mixtures, thereof. Differentiation agents which can be used in the present invention are detailed in "Marrow-mindedness: a perspective on neuropoiesis", by Bjorn Scheffler, et al., TINS, 22, pp. 348–356 (1999), which is incorporated by reference herein.

The term "neurodegenerative disease" is used throughout the specification to describe a disease which is caused by damage to the central nervous system and which damage can be reduced and/or alleviated through transplantation of neural cells according to the present invention to damaged areas of the brain and/or spinal cord of the patient. Exemplary neurodegenerative diseases which may be treated using the neural cells and methods according to the present invention include for example, Parkinson's disease, Huntington's disease, amyotrophic lateral sclerosis (Lou Gehrig's disease), Alzheimer's disease, Rett Syndrome, lysosomal storage disease ("white matter disease" or glial/demyelination disease, as described, for example by Folkerth, J. Neuropath. Exp. Neuro., 58, Sep. 9, 1999), including Sanfilippo, Tay Sachs disease (beta hexosaminidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of said patient or which has occurred from physical injury to the brain and/or spinal cord. The term neurodegenerative diseases also includes neurodevelopmental disorders including for example, autism and related neurological diseases such as schizophrenia, among numerous others.

Selecting for umbilical cord pluripotential stem and/or progenitor cells according to the present invention can be done in a number of ways. For example, the cells may be selected using, for example a magnetic cell separator (FACS) or other system which removes all cells which contain a CD marker and then the remaining cells may be expanded in growth medium or differentiated in growth medium which includes a differentiation agent. Alternatively, an enriched population of stem and/or progenitor cells may be obtained from a sample of mononuclear cells by subjecting the cells to an agent such as Ara-C or other anti-proliferative agent such as methotrexate, which causes the death of proliferating cells within a sample (the stem and/or progenitor cells are non-proliferating and are unaffected by the agent). The remaining cells may then be grown in a cell culture medium which contains a mitogen to produce a population of differentiated and quiescent cells, which cell population may be further grown to concentrate the quiescent cells to the effective exclusion of the differentiated cells (the quiescent cells in the final cell medium will greatly outnumber the original differentiated cells which do not grow in the medium). The quiescent cells may then be induced to adopt a number of different neural phenotypes, which cells may be used directly in transplantation.

Additional in vitro differentiation techniques can be adapted through the use of various cell growth factors and co-culturing techniques known in the art. Besides co-culturing with fetal mesencephalic or striatal cells, a variety of other cells can be used, including but not limited to accessory cells, and cells from other portions of the fetal and mature central nervous system.

The term "gene therapy" is used throughout the specification to describe the transfer and stable insertion of new genetic information into cells for the therapeutic treatment of diseases or disorders. The foreign gene is transferred into a cell that proliferates to spread the new gene throughout the cell population. Thus, stem cells, or pluripotent progenitor cells according to the present invention either prior to differentiation or preferably, after differentiation to a neural cell phenotype, are the target of gene transfer, since they are proliferative cells that produce various progeny lineages which will potentially express the foreign gene.

The following written description provides exemplary methodology and guidance for carrying out many of the varying aspects of the present invention.

General Methods

Standard molecular biology techniques known in the art and not specifically described are generally followed as in Sambrook et al., Molecular Cloning: A Laboratory Manual, Cold Springs Harbor Laboratory, New York (1989, 1992), and in Ausubel et al., Current Protocols In Molecular Biology, John Wiley and Sons, Baltimore, Md. (1989). Polymerase chain reaction (PCR) is carried out generally as in PCR Protocols: A Guide To Methods and Applications, Academic Press, San Diego, Calif. (1990). Reactions and manipulations involving other nucleic acid techniques, unless stated otherwise, are performed as generally described in Sambrook, et al., 1989, Molecular Cloning: a Laboratory Manual, Cold Springs Harbor Laboratory Press, and methodology as set forth in U.S. Pat. Nos. 4,666,828; 4,683,202, 4,801,531; 5,192,659; and 5,272,057 and incorporated herein by reference. In-situ PCR in combination with Flow Cytometry can be used for detection of cells containing specific DNA and mRNA sequences (see, for example, Testoni et al. Blood 87:3822 (1996)).

Standard methods in immunology known in the art and not specifically described are generally followed as in Stites et al. (eds), BASIC AND CLINICAL IMMUNOLOGY, 8'th Ed., Appleton & Lange, Norwalk, Conn. (1994); and Mishell and Shigi (eds), Selected Methods In Cellular Immunology, W. H. Freeman and Co., New York (1980).

Immunoassays

In general, immunoassays are employed to assess a specimen such as for cell surface markers or the like. Immunocytochemical assays are well known to those skilled in the art. Both polyclonal and monoclonal antibodies can be used in the assays. Where appropriate other immunoassays, such as enzyme-linked immunosorbent assays (ELISAs) and radioimmunoassays (RIA), can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 2o 4,879,219; 5,011,771 and 5,281,521 as well as Sambrook et al., Molecular Cloning: A Laboratory Manual, Cold Springs Harbor, N.Y. (1989). Numerous other references also may be relied on for these teachings.

Antibody Production

Antibodies may be monoclonal, polyclonal or recombinant. Conveniently, the antibodies may be prepared against the immunogen or immunogenic portion thereof, for example, a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, Antibodies: A Laboratory Manual, Cold Spring Harbor Laboratory, Cold Springs Harbor, N.Y. (1988) and Borrebaeck, Antibody Engineering- A Practical Guide by W.H. Freeman and Co. (1992). Antibody fragments may also be prepared from the antibodies and include Fab and F(ab')2 by methods known to those skilled in the art. For producing polyclonal antibodies a host, such as a rabbit or goat, is immunized with the immunogen or immunogenic fragment, generally with an adjuvant and, if necessary, coupled to a carrier; antibodies to the immunogen are collected from the serum. Further, the polyclonal antibody can be absorbed such that it is monospecific. That is, the serum can be exposed to related immunogens so that cross-reactive antibodies are removed from the serum rendering it monospecific.

For producing monoclonal antibodies, an appropriate donor is hyperimmunized with the immunogen, generally a mouse, and splenic antibody-producing cells are isolated. These cells are fused to immortal cells, such as myeloma cells, to provide a fused cell hybrid that is immortal and secretes the required antibody. The cells are then cultured, and the monoclonal antibodies harvested from the culture media.

For producing recombinant antibodies, messenger RNA from antibody-producing B-lymphocytes of animals or hybridoma is reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system. Antibody cDNA can also be obtained by screening pertinent expression libraries. The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice,* Blackwell Scientific Publications, Oxford, 1982). The binding of antibodies to a solid support substrate is also well known in the art. (see for a general discussion Harlow & Lane, *Antibodies: A Laboratory Manual,* Cold Spring Harbor Laboratory Publications, New York, 1988 and Borrebaeck, *Antibody Engineering—A Practical Guide,* W.H. Freeman and Co., 1992). The detectable moieties contemplated with the present invention can include, but are not limited to, fluorescent, metallic, enzymatic and radioactive markers. Examples include biotin, gold, ferritin. alkaline phosphates, galactosidase, peroxidase, urease, fluorescein, rhodamine, tritium, $^{14}C$, iodination and green fluorescent protein.

Gene Therapy

Gene therapy as used herein refers to the transfer of genetic material (e.g., DNA or RNA) of interest into a host to treat or prevent a genetic or acquired disease or condition. The genetic material of interest encodes a product (e.g., a protein. polypeptide. and peptide, functional RNA, antisense) whose in vivo production is desired. For example, the genetic material of interest encodes a hormone, receptor, enzyme, polypeptide or peptide of therapeutic value. Alternatively, the genetic material of interest encodes a suicide gene. For a review see "Gene Therapy" in *Advances In Pharmacology,* Academic Press, San Diego, Calif., 1997.

Administration of Cells for Transplantation

The cells of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art.

In the method of the present invention, the cells of the present invention can be administered in various ways as would be appropriate to implant in the central nervous system, including but not limited to parenteral, including intravenous and intraarterial administration, intrathecal administration, intraventricular administration, intraparenchymal, intracranial, intracisternal, intrastriatal, and intranigral administration. In addition, all of these routes of administration may be used to effect transplantation of neural cells in the present invention.

Methods of treating a patient for a neurodegenerative disease or brain and/or spinal cord damage caused by, for example, physical injury or by ischemia caused by, a stroke, heart attack or cardiovascular disease comprise administering neural cells to said patient in an amount sufficient to effect a neuronal transplantation. One of ordinary skill may readily recognize that one may use treated (i.e., cells exposed to at least one differentiation agent) or untreated neural cells for such methods, including fresh umbilical cord blood or a mononuclear fraction thereof.

Pharmaceutical compositions comprising effective amounts of treated neural cells are also contemplated by the present invention. These compositions comprise an effective number of treated neural and/or neuronal and/or glial cells, optionally in combination with a pharmaceutically acceptable carrier, additive or excipient. In certain aspects of the present invention, cells are administered to the patient in need of a transplant in sterile saline. In other aspects of the present invention, the cells are administered in Hanks Balanced Salt Solution (HBSS) or Isolyte S, pH 7.4. Other approaches may also be used, including the use of serum free cellular media. Such compositions, therefore, comprise effective amounts or numbers of treated neural cells in sterile saline. These may be obtained directly by using fresh or cryopreserved umbilical cord blood or alternatively, by separating out the mononuclear cells (MNC) from the whole blood, using density gradient separation methods, among others, which are well known in the art (one such approach is presented herein). The isolated MNC may be used directly for administration/transplantation or may be treated with at least one differentiation agent and used without further purification or isolation of neural cells, or alternatively, after treatment with at least one differentiation agent, the neural cells may be isolated and used. Intravenous or intraarterial administration of the cells in sterile saline to the patient may be preferred in certain indications, whereas direct administration at the site of or in proximity to the diseased and/or damaged tissue may be preferred in other indications.

Pharmaceutical compositions according to the present invention preferably comprise an effective number within the range of about $1.0 \times 10^4$ mononuclear cells to about $5.0 \times 10^7$ mononuclear cells, more preferably about $1 \times 10^5$ to about $9 \times 10^6$ mononuclear cells, even more preferably about $1 \times 10^6$ to about $8 \times 10^6$ cells generally in solution, optionally in combination with a pharmaceutically acceptable carrier, additive or excipient. Effective numbers of neural cells, either within a sample of mononuclear cells or as concentrated or isolated neural cells, may range from as few as several hundred or fewer to several million or more, preferably at least about one thousand cells within this range. In aspects of the present invention whereby the cells are injected in proximity to the brain or spinal cord tissue to be treated, the number of cells may be reduced as compared to aspects of the present invention which rely on parenteral administration (including intravenous and/or intraarterial administration).

In using compositions according to the present invention, fresh or cryopreserved umbilical cord blood, a mononuclear fraction thereof, or fractions wherein neural cells are isolated and/or concentrated (using FACS or other separation methods for isolating neural cells from a population of mononuclear cells) may be used without treatment with a differentiation agent or with an effective amount of a differentiation agent prior to being used in a neuronal transplant. In one preferred aspect of the present invention, a mononuclear fraction of cord blood is exposed to effective amounts of at least one differentiation agent (in cell media) for a period to effect differentiation of cord stem cells into cells which express a neuronal and/or glial phenotype and after such period, these cells are then used to effect a transplant in a patient.

In aspects of the invention in which cord blood stem cells are differentiated, the use of standard media which has been supplemented with at least one or more differentiation agent is preferred. A combination of retinoic acid and nerve growth factor (NGF) in effective amounts in certain aspects of the present invention as the differentiation agent is preferred. In certain preferred aspects of the present invention, neural cells are prepared from cord blood stems cells growing in standard growth media in a two step approach using neural proliferation media followed by a differentiation media. In this aspect of the present invention, cells grown in standard cellular media (preferably, at least a minimum essential medium supplemented with non-essential amino acids, glutamine, mercaptoethanol and fetal bovine serum (FBS)) are initially grown in a "neural proliferation medium" (i.e., a medium which efficiently grows neural cells) followed by growth in a "differentiation medium") (generally, similar to the neural proliferation medium with the exception that specific nerve differentiation agents are added to the medium and in certain cases, other growth factors are limited or removed). A preferred neural proliferation medium is a media which contains DMEM/F12 1:1 cell media, supplemented with 0.6% glucose, insulin (25 µg/ml), transferrin (100 µg/ml), progesterone 20 nM, putrescine (60 µM, selenium chloride 30 nM, glutamine 2 mM, sodium bicarbonate 3 mM, HEPES 5 mM, heparin 2 µg/ml and EGF 20 nm/ml, bFGF 20 ng/ml. One of ordinary skill will readily recognize that any number of cellular media may be used to provide appropriate neural proliferation medium and/or differentiation medium.

The following examples are provided to illustrate or exemplify certain preferred embodiments of the present invention illustrative of the present invention but are not intended in any way to limit the present invention.

EXAMPLES

Preparation of Cellular Samples

Cryopreserved or fresh umbilical cord blood (from human or rat umbilical cord that remains attached to placenta after delivery) is harvested and processed by Ficoll centrifugation. This results in nearly 100% recovery of mononuclear cells which can be a) grafted directly into a region of injured brain (eg in a rat stroke model or model of neurodegenerative disease or trauma model) b) processed into sub-populations based on surface markers or c) cryopreserved for later use. Initial experiments with umbilical cord blood utilize all of the mononuclear cells collected, without separation of CD34+ cellular components (hematopoietic stem cells). Other experiments utilize cord blood that is depleted of CD34+ cells as described below. Approximately 100,000 to 90,000,000 ($1 \times 10^5$ to about $9 \times 10^7$, preferably at least about $1 \times 10^6$) cord blood cells are injected into the hemisphere rendered ischemic by acutely obstructing blood flow to cerebral cortex. Assessment of recovery of limb function in the rat model of stroke is performed at 2 and 4 and 8 weeks after grafting.

Preparation of Cord Blood Devoid of Hematopoietic Stem Cells (CD34+)

Using a magnetic cell sorting kit (Milteny Biotec, Inc, Auburn Tex.), cord cells are labeled with CD34+ microbeads which marks cells that express hematopoietic stem cell antigen (CD34 in human samples). The cord blood cells are passed through an MS+ column for selection of CD34+ cells. Two hundred µL of CD34+ Multi-sort MicroBeads is added per $10^8$ total cells, mixed and incubated for 15 min at 6–12° C. Cells are washed by adding 5–10× the labeling volume of buffer, centrifuged for 10 min at 200×g and supernatant is removed. The cell pellet is resuspended in 500 µL buffer. The MS+/RS+ column is washed with 500 µL of buffer. The cell suspension is applied to the column and the "negative" cells passed through. The negative cells contain all cells in the cord blood except the hematopoietic CD34+ cells. The column is then rinsed with 500 µL of buffer three times. These washing are added to the "negative" cell fraction, centrifuged for 10 min at 220×g and the supernatant removed. The cell pellet is resuspended in 500 µL of buffer and diluted 1:1 with Dulbecco's Minimal Essential Media (DMEM, GIBCO/BRL) and 10% fetal bovine serum (FBS), centrifuged through a density gradient (Ficoll-Paque Plus, 1.077 g/ml, Pharmacia) for 30 min at 1,000×g. The supernatant and interface are combined and diluted to approximately 20 ml with growth medium and plated in polyethylene-imine coated plastic flasks.

Defining the Optimal Medium For Generating Cord Blood Clones

The cord blood is suspended in serum-free medium composed of a 1:1 mixture of Dulbecco's Minimal Essential Media (DMEM) and F12 nutrient (Life Technologies-BRL). Other samples of cord blood material are suspended in DMEM+10% Fetal Bovine Serum (FBS). The defined culture medium is composed of DMEM/F12 (1:1) including glucose, glutamine, sodium bicarbonate and HEPES buffer plus a defined hormone and salt mixture (see Daadi and Weiss, 1999). To identify the optimal cell density for cell survival and growth, cells are plated at densities varying from 50,000 to $3 \times 10^6$ cell/ml in Corning T75 culture flasks in the defined media together with a specific mitogenic growth factor(s) (see below for the mitogens used). Cell survival and proliferation are monitored very closely by examining culture flasks, noting and counting clones that arise daily. After a fixed culture period of 10 days the total number of clones are counted in both serum free and serum supplemented cultures and compared. This gave us the number of precursor cells able to generate clones and rate of proliferation. Then these clones are harvested, dissociated and the total viable cells counted and reseeded for a second passage and so on for the future passages. This last count allowed determination of the rate of proliferation and the size of clones generated under each condition.

Caveats: From our experience with neural stem cells, we have found that exposure of cells to serum induces differentiation and inhibits proliferation of neural lineages. Lower cell density also does not favor cell proliferation. Therefore, it is likely that we will observe variability in the rate of cell growth depending on the presence and absence of serum, the cell density and mitogen used. The media composition may not be optimal for cell survival, proliferation and enrichment for a neural cell population. We also see differences in morphologies and antigens expressed by the cells under these two separate conditions. Therefore, before each passage we identify the total number of clones and cells and also the proportion of neurons, astrocytes and oligodendrocytes as well as hematopoietic cell lineages. These data will guide us to constantly improve our medium formula by trying new media components and, if necessary, a very low percentage of Bovine Serum Albumin (BSA) or neural stem cell conditioned media.

Identification of Sub-Populations of Cord Blood Cells Responsive to Specific Mitogens and which Express Specific Neural Markers The cord blood suspension is plated at an optimal cell density in corning T75 culture flasks in the optimal medium (as described above). This medium is supplemented with 10 to 20 ng/ml of one or a combination of a variety of growth factors that have been shown to exert mitogenic actions on neural and mesenchymal precursors. These growth factors are: Epidermal Growth Factor (EGF) family ligands (EGF, Transforming Growth Factor α, amphiregulin, betacellulin, heparin-binding EGF and Heregulin), basic Fibroblastic growth factors (bFGF) and other members of its superfamily (FGF1, FGF4), members of Platelet-Derived Growth Factor family (PDGF AA, AB, BB), Interleukins, and members of the Transforming Growth Factor β superfamily. After a period of 10 to 15 days in vitro, the cells are harvested and then reseeded in fresh medium containing growth factor(s). To identify their immature nature, some of these cells are plated on poly-L-ornithine-coated glass coverslips in 24-well Nunclon culture dishes. After, a period of 30 minutes to 1 hour these cells are fixed with 4% paraformaldehyde and stained with a variety of markers for immature cells such as Nestin, vimentin, the CD markers CD34 (marker of hematopoietic stem cell) and CD33 and dendritic cell markers. The rest of the cells are reseeded in growth medium (medium containing mitogens) for the next passage. For each growth factor used cell survival and proliferation is closely monitored and clones that arise every day are counted and the total number of clones formed after a fixed period is determined. We also determine the proportion of cell types generated under each mitogen, as described below.

Different rates of cell proliferation and/or proportion of cell types are generated depending on the growth factor used and its concentration. Neuronal differentiation efficacy and the number of passages able to be carried out under each mitogen is determined. Studies have shown that the combination of EGF and FGF is required to isolate and propagate human neural stem cell. Therefore we test combinations of these growth factors and potentiated the mitogenic action by adding a specific component (heparin when bFGF is used as the mitogen).

Establishment of Multipotent Clonally Derived Sub-Populations of Cord Blood Stem Cells.

Isolation of precursor sub-populations based on their response to epigenetic signals generate a homogeneous cell population that behave in a predictable and similar manner when transplanted in vivo or challenged with a specific treatment in vitro. These clonal cell lines are good candidates for clinical-grade development. From the initial starting growth factor responsive population of stable human cord blood cells, monoclonal cell populations are established as previously described (Daadi and Weiss, J. Neurosci. 19, 11 4484, 1999). Clusters of cells are dissociated, counted and suspended in media-hormone mix at a concentration of 1 cell per 15 µl and plated at 15 µl/well in Terasaki microwells or a 96-well dish. Wells with single cells are immediately identified and marked. Single cells are also randomly picked from the suspension using a hand-pulled 10 µl micropipette and transferred into a Terasaki microwell containing 10–15 µl of media. Clonal development is monitored once per day using the inverted microscope with phase-contrast optics. Cultures are fed by replacing 2 µl with fresh medium every 2 days.

Each single cell proliferates and generates a clone of cells. A fraction of these single founder cells have a slow growth rate or do not proliferate or even die after a few days in culture. From our experience with neural stem cells and using clonal cultures, some single cells may undergo cell death because of the lack of neighboring cells that provide extracellular support for cell survival and in specific cases cell division. If this is a problem, the founder cell are cultured in conditioned medium derived from bulk stem cell cultures, or in the presence of the membrane extract of cord blood cells.

Characterization and Determination of the Differentiation Efficacy of each Clone.

In addition to growing a purified monoclonal human cord blood-derived stem cell populations, it is necessary to verify that each generation of the clone exhibits all stem cell characteristics i.e.: ability to self renew, generate a large number of progeny and be able to respond to environmental cues and differentiate into different cell types. These efficacy criteria are fundamental for the development and the production of stable multipotent clones. Clonally derived cells (as described above) are dissociated either by gentle mechanical trituration or using trypsin-EDTA. After the growth phase, part of the next generation clone is cultured under differentiation conditions. When cells grow as a cluster in suspension each clone is removed and plated in control media-hormone mixture without any mitogens on a glass coverslip coated with an extracellular matrix (ECM). Different ECMs including laminin, Poly-L-ornithine and poly-D-lysine are tested for their potential differentiation effects. If cells grow as a monolayer, media containing the mitogen is removed by gentle suction and replaced by control fresh media (no mitogen). After a culture period of 10 to 15 days, differentiated cells are fixed with paraformaldehyde and stained for various neural and, hematopoietic cell markers. Analysis of labeled subpopulation are carried out using immunocytochemical techniques and Flow Cytometric Analysis. For neural lineages we use: anti-Nestin, and anti-Vimentin to label immature precursor cells; anti-Glial Fibrillary Acidic Protein to label Astrocytes, anti-O4, anti-Myelin Basic Protein and anti-CNPase to identify oligodendrocytes, Anti-NeuN, Anti-β-tubulin class III, Anti-Neuron Specific Enolase, Anti-human specific Neurofilament, Anti-MAP2 to identify neurons. Within this last neuronal population we test for different neurotransmitter phenotype expression like GABA, Choline Acetyltransferase, Tyrosine Hydroxylase and Serotonin. We also test for hematopoietic cells: Some of the characterized multipotent stem cell clones are cryopreserved as described in general methods section (see below) and the rest passaged and maintained in culture.

Cryopreservation

Clonally derived cord blood cells are resuspended in cell freezing media comprising 10% dimethyl sulfoxide, 50% Fetal Bovine Serum and 40% of defined medium and stored under liquid nitrogen are well known in the art.

The mononucleoar layer from whole umbilical cord blood may be prepared for cryopreservation using the following methodology, which steps may be varied without significantly changing the cryopreservation outcome.

Processing and Storage of Umbilical Cord Blood

1. Sample Preparation

Anticoagulated cord blood is aliquotted into sterile 50 ml conical tubes and the volume measured accurately. A small sample is removed for white cell count and sterility testing. A sample of plasma is removed at this time by centrifugation for cryopreservation. The cord blood is diluted 1:2 with sterile phosphate buffered saline (PBS) and mixed carefully to a maximum of 35 ml per tube.

Step 2: Density Gradient Separation

Mononuclear cells are obtained from the cord blood using Ficoll-Hypaque density centrifugation. Each tube of diluted cord blood is underlayered with 10 ml of sterile Ficoll-Hypaque solution and then centrifuged at 1200 g for 30 min. at room temperature. In this procedure, mononuclear cells containing progenitor cells (stem cells) form a layer at the Ficoll/plasma interface whereas red cells and granular cells (granulocytes) pass through the gradient to the bottom of the tube. The mononuclear cells are removed carefully by aspiration.

Step 3: Mononuclear Cell Preparation (MNC)

The mononuclear cells are collected in sterile 50 ml tubes and diluted 1:2 with tissue culture medium (RPMI) and centrifuged at 1500 g for 15 minutes. The cells are further washed in RPMI and resuspended to a fixed volume (14 ml) and a small sample removed for white cell enumeration and CD34+ cell determination.

Step 4: Preparation of MNC for Cryopreservation

The cell suspension is then centrifuged at 1200 g for 10 mins and the cells resuspended in 2.5 ml of RPMI. A small sample is removed for sterility testing. To this suspension. 2.5 ml of autologous plasma containing 10% dimethyl sulfoxide (DMSO) as cryoprotectant is added slowly and the resulting suspension transferred to a labeled (bar coded) sterile, 5 ml cryovial.

Step 5: Controlled Rate Freezing in Liquid Nitrogen

The samples are then cryopreserved using a controlled rate of freezing from 4 deg C. to −90 deg C. using the following protocol:
+4 degree C. to −3 degree C. at one degree C. per minute
−3 degree C. to −20 degree C. at 10 degree C. per minute
−20 degree C. to −40 degree C. at one degree C. per minute
−40 degree C. to −90 degree C. at 10 degree C. per minute.

The cryovials are then stored in vapor phase of liquid nitrogen at −196 degrees C.

Differentiating Culture Conditions

Three T75 flasks of 10–15 days old suspension cultures are spun down for 5 min at 400 rpm. The cells are removed and placed into a 12 ml centrifuge tube and spun down for 5 min at 600 rpm. The growth medium is removed, and cells resuspended in fresh control media (no EGF or other mitogen) plus hormone mix. This step is repeated one more time to ensure the complete removal of the mitogen from the media. Dissociated cells are plated in media hormone mix at a density of $1 \times 10^6$ cells/ml on poly-L-ornithine-coated (15 μg/ml; Sigma) glass coverslips in 24-well Nunclon culture dishes with 0.5 ml/well. After 7 to 14 days in culture, cells will change morphology into a neuron-like or glial-like phenotype. Following staining with specific antibodies which recognize markers of neural precursors, of neurons and of glia, the differentiation efficacy of the hormone mix is quantified. The density of positively stained cell bodies are determined in at least 20 randomly selected fields from each culture dish or well using the 40× objective. For quantitation of total NeuN-ir, GFAP and nestin-ir cells produced, a total of 3 experiments are performed resulting in total of 6 culture dishes or wells analyzed for each condition. Neural differentiation efficacy of a growth factor (or hormone mixture) are calculated as the percentage of NeuN-immunoreactive cells (relative to total number of cells in a dish identified with DAPI nuclear stain).

Indirect Immunocytochemistry

Rabbit polyclonal antisera and mouse monoclonal antibodies directed against specific antigens are used as primary antibodies for indirect immunofluorescence. Coverslips fixed with 4% paraformaldehyde for 20 min followed by three washes (10 min each) in phosphate buffer saline (PBS). After the PBS rinse, coverslips are processed for single or dual labeling and incubated with primary antibodies generated from different species. The primary antibodies are made in PBS/10% normal goat serum+0.3% triton X-100. After 2 hours incubation at 37° C., the coverslip are rinsed in PBS. Fluorescent conjugated secondary antibodies (1:100, 1:200, Jackson ImmunoResearsh) are applied in PBS for 30 min at room temperature. Coverslips are then washed three times (10 min each) in PBS, rinsed with water, placed on glass slides, and coverslipped using Fluorsave (Calbiochem). Fluorescence is detected and photographed using Zeiss Laser Scanning Confocal microscope (model LSM 510). The primary antibodies that are used are against: Nestin (1:1000; PharMingen), Vimentin (1:200, Boehringer), Glial Fibrillary Acidic Protein (1:500, Sigma), O4 (1:100, Chemicon), Myelin Basic Protein (1:200, Boehringer), and CNPase (1:500, Sternberger Monoclonals), NeuN (1:100, Chemicorp), β-tubulin class III (1:1000, Sigma), Neuron Specific Enolase (1:100, Chemicon), human specific Neurofilament (1:150, Boehringer), MAP2 (1:200, Chemicon), GABA (1:5000, Sigma), Choline Acetyltransferase (1:200, Chemicon), Tyrosine Hydroxylase (1:4000, Incstar), Serotinin (1:200, Chemicon), type IV collagen (1:50, Dako), Laminin (1:300, Sigma), CD10 (1:100, PharMingen), muscle actin (1:1000, Sigma), HLA-DR (1:200, PharMingen), CD45 (1:100, PharMingen), Mac-1 (1:100, Chemicon); alkaline phosphatase staining kit (Sigma #85L-2).

Flow Cytometric Analysis

To assess the actions of specific treatment on differentiation or to establish a relative profile within a culture condition of different cell populations labeled with the markers mentioned above, the harvested cells are subject to Flow Cytometric Analysis. Cells are rinsed with fluorescence activated cell sorting (FACS) buffer (EBSS and 1% HIFBS) and $1 \times 10^6$ cells are added to 100 µl of FACS buffer supplemented with the appropriate primary antibodies and incubated at 4° C. for 30 min. After washing, secondary antibodies are added and incubated at 4° C. for 30 min. For biotinylated antibodies, isotype controls are used to set gates; otherwise, gates are set with cells alone. Cell viabilityis monitored using propidium iodide exclusion. Flow Cytometric Analysis is performed with FACScan™ (Becton-Dickinson) with all events gated on the forward and side scatter.

Western Blotting

The culture is washed three times in cold phosphate buffered saline (PBS), scraped into ice-cold PBS, and lysed in ice-cold lysis buffer containing 20 nM Tris/HCl (pH=8.0), 0.2 mM EDTA, 3% Nonidet P-40, 2 mM orthovanadate, 50 mM NaF, 10 mM sodium pyrophosphate, 100 mM NaCl, and 10 µg each of aprotinin and leupeptin per ml. After incubation on ice for 10 min, the samples are centrifuged at 14,000×g for 15 min and supernatants are collected. An aliquotis removed for total protein estimation (bio-Rad assay). An aliquot corresponding to 10 µg of total protein of each sampleis separated by SDS/PAGE (10%) under reducing conditions and transferred electrophoretically to nitrocellulose filters. Nonspecific binding of antibody is blocked with 5% non-fat dry milk overnight at 4° C. Immunoblottingis carried out with the appropriate primary antibody followed by their corresponding peroxidase conjugated secondary antibodies. The blots are developed by enhanced chemiluminescence method (ECL, Amersham).

Reverse transcription-polymerase chain reaction (RT-PCR) and Northern analysis Total RNA is extracted using TRIzol (Life Technologies-BRL) according to the recommended protocol.

RT-PCR: aliquot of 1 µg of RNA is reverse-transcribed in the presence of 50 mM Tris-HCL, pH 8.3, 75 mM KCL, 3 mM MgCl2, 10 mM DTT, 0.5 mM dNTPs and 0.5 µg Oligo-dT (12–18) (Pharmacia) with 200 U Superscript Rnase H-Reverse Transcriptase (Life Technologies-BRL). Aliquots of cDNA equivalent to 40 ng of total RNA are amplified in 25 µl reactions containing 10 mM Tris-HCl, pH 8.3, 50 mM KCl, 1.5 mM MgCl2, 50 pmol of each primer, 400 µM dNTPs, and 0.5 U AmpliTaq DNA polymerase (Perkin-Elmer). The PCR thermal profileis determined for each pair of primer sequence used.

Southern blot. 15 µl aliquots of the amplified PCR products are run on a 2% agarose Tris-acetate gel containing 0.5 µg/ml ethidium bromide. The bands are transferred by capillary action to a Hybond-N+ membrane and detected using the appropriate radiolabeled probes. The radioactive membrane is exposed overnight to a BioMaxMR autoradiographic film (Kodak) at −80° C.

Northern hybridization. Aliquots (20 µg) of total RNA are fractioned on agarose formaldehyde gels. The RNAis transferred by capillary action from the gel matrix to Hybond-N+ (Amersham) using 10×SSC, and fixed onto membrane by baking. These membranes are hybridized with the adequate radio-labeled probes, washed with decreasing concentration of SSC, 0.1% SDS and exposed to a BioMaxMR autoradiographic film for 24 hours (Kodak) at −80° C.

Human Umbilical Cord Blood Contains Multi-Potent Progenitor Cells which Give Rise to Neural Lineage General Methods Following the methods which are generally set forth above, cord blood was shown to contain cells which can differentiate to neural cells.

Source of Cells

The mononuclear cells for this study were isolated from human umbilical cord blood samples. The cord blood samples were obtained from the stump of the umbilical cord on the placental side postpartum. Between 50 and 100 ml of blood was obtained per procedure. Cells were spun down, resuspended in crypopreservative medium and frozen in liquid nitrogen until needed.

Handling of the Cells and Culture Media. The frozen cells were thawed, spun down, resuspended and plated in 75 mm culture flasks in minimal essential medium (DMEM) supplemented with 2 mM glutamine(100× stock from Gibco/BRL), 0.001% B-mercaptoethanol, 1× non-essential amino acids (100× stock from Gibco/BRL) and 10% FBS (stem cell qualified, Gibco/BRL). After 24 to 72 hrs, the medium was replaced with serum free "Neural Proliferation Medium" which consisted of "N2" medium (DMEM/F12 1:1, Gibco/BRL) supplemented with 0.6% glucose, insulin 25 ug/ml, transferrin 100 ug/ml, progesterone 20 nM, putrescine 60 uM, selenium chloride 30 nM, glutamine 2 mM, sodium bicarbonate 3 mM, HEPES 5 mM, heparin 2 ug/ml and EGF 20 ng/ml, bFGF 20 ng/ml. Differentiation medium consisted of the "Neural Proliferation Medium" without the EGF and bFGF, but instead containing retinoic acid (0.5 µM) plus 100 ng/ml nerve growth factor (NGF). Detection of proliferating cells was accomplished by incubating cultures with bromodexoyuridine (BrdU) (5 µM) for 24–48 hrs with subsequent visualization of BrdU immunoreactive cells.

Isolation of RNA. Total RNA was isolated from human cord blood cells (or fractions thereof) using the RNA STAT-60 kit using the protocol recommended by the manufacturer (Tel-Test "B", Inc. Friendswood, Tex. 77546). Following RNA isolation, its OD density was measured at 260 nm, and stored at −80° C. Integrity was tested on 1% non-denaturing Seakem LE agarose gel (FMC Bioproducts, Rockland, Me.).

DNA Microarray

Total RNA was prepared as above. Total RNA obtained from human cord blood cells, with or without RA+NGF treatment from different batches were pooled together for this experiment (15 to 20 g total RNA was needed per chip). The human genome U95A array (HG-U95A) from Affymetrix Inc. was used in this experiment. The single array represents ~12,500 sequences. The experiment was done at the Functional Genomics Core, Microarray Facility at the H. Lee Moffitt Cancer Center & Research Institute using Gene-Chip Fluidics station 400, a GeneChip Hybridization oven, and an HP GeneArray™ scanner. Analysis of the GeneChip microarray hybridization pattern was performed using GeneChip Analysis Suite 4.0 software.

Reverse Transcription (RT). RT was performed using random hexamers as primers. Final volume was 20 µl with 1 µg of total RNA from each fraction of cells. The reaction mixture contained 1 mM of each deoxynucleoside triphosphate (dNTP), 1 U/µl RNase inhibitor, 5 mM $MgCl_2$, 2.5

U/μl Murine leukemia virus (MuLV) reverse transcriptase, 2.5 μM random hexamers in 50 mM KCl and 10 mM Tris-HCl (pH 8.3). It was first incubated at room temperature for 10 min, and then at 42° C. for 15 minutes. The mixture was then be heated at 99° C. for 5 minutes and cooled on ice for 5 min to inactivate the transcriptase.

Polymerase Chain Reaction (PCR). PCR was performed in the same tubes as RT, in 100 μl total volume. Final concentrations were 2 mM MgCl$_2$, 0.2 mM of each dNTP, and 2.5 U/100 μl Ampli Taq DNA polymerase in the 50 mM KCl and 10 mM Tris-HCl buffer (pH 8.3). For generation of various cDNA fragments, a PE 9700 thermocycler (Perkin Elmer, Foster City, Calif.) was programmed as follows: 1 cycle at 95° C. for 105 sec, 35 cycles at 95° C. for 15 sec, followed by 60° C. for 30 sec, and finally 1 cycle at 72° C. for 7 min. Both RT and PCR was done using Perkin Elmer's GeneAmp RNA PCR kit. To identify the presence of various neuronal markers, primers were constructed based on published human sequences. For Nestin (accession #X65964), forward primer: nt 2524–2542 and reverse primer: nt 2921–2903. For Musashi-1 (accession #AB012851), forward primer: nt 319–339 and reverse primer: nt 618–598. For Necdin (accession #AB007828), forward primer: nt 2374–2393 and reverse primer: nt 2767–2747. For Neurofilament subunit NF-L (accession #X05608), forward primer: nt 3155–3173 and reverse primer: nt 3521–3501. Primers were selected using the SEQWEB (version 1.1) software available on the USF computer network.

Antibodies

The primary antibodies used included: Musashi-1 (donated by Prof. H. Okano), Nestin (1:200, Chemicon); NeuN (1:100, Chemicon), class III β-tubulin (1:200, Sigma); GFAP (1:500, Sigma), BrdU (1:400, Chemicon), MAP2 (1:200, Chemicon), pleiotrophin (1:400, R&D Systems).

Western Blot. Cultures were processed using standard methods for performance of Western blot analysis using the following procedure. Cultures were washed three times in cold phosphate buffered saline (PBS), scraped into ice-cold PBS, and lysed in ice-cold lysis buffer containing 20 nM Tris/HCl (pH 8.0), 0.2 mM EDTA, 3% Nonidet P-40, 2 mM orthovanadate, 50 mM NaF, 10 mM sodium pyrophosphate, 100 mM NaCl, and 10 μg each of aprotinin and leupeptin per ml. After incubation on ice for 10 min, the samples were centrifuiged at 14,000×g for 15 min and supernatants were collected. An aliquot was removed for total protein estimation (Bio-Rad assay). An aliquot corresponding to 10 μg of total protein of each sample was separated by SDS/PAGE (10%) under reducing conditions and transferred electrophoretically to nitrocellulose filters. Nonspecific binding of antibody was blocked with 5% non-fat dry milk overnight at 4 C. The blots were analyzed using the Kodak DS 1D Digital Science Electrophoresis Documentation and Analysis System 120 v.0.2.

Immunocytochemistry After 7–14 DIV, the cultures was fixed with 4% paraformaldehyde in 0.1 M phosphate buffer (PB) for 20 minutes. The cultures were then washed 3 times with phosphate buffered saline prior to beginning immunocytochemistry.

Cell Counts For estimates of cell number in culture, 20 random visual fields (40× objective) in 4 culture dishes for each marker were viewed. The total number of cells visualized under phase contrast microscopy and the number of positively labeled (immunoreactive) cells was counted in each visual field. The mean number of labeled cells was then expressed as a percentage of the total number of cells per field.

Results

Cord blood cells, cultured in the presence and absence of retinoic acid (RA) and Nerve Growth Factor (NGF), gave rise to cells bearing neural progenitor markers as evidenced by profiles of gene and protein expression. A total of 322 genes were either up- or down-regulated by a factor of at least 2, evidenced by measurements using a human microarray "gene chip." The greatest degree of up-regulation (44-fold increase) was seen in the mRNA for neurite outgrowth extension protein or pleiotrophin. A significant degree of down-regulation was seen in the expression of tenascin (decreased 8.8 fold), an extracellular matrix protein that inhibits neurite outgrowth in developing neuronal tissues, and in fibronectin (decreased 5.8 fold), an extracellular matrix protein that favors development of blood cell lineages. Other transcripts associated with neurogenesis that increased significantly (>2 fold) include glypican-4 (increased 4.9 fold), neuronal pentraxin II (increased 2.3 fold), neuronal growth associated protein 43 (increased 2.7 fold), and neuronal PAS1 (increased 2.3 fold). Musashi-1 was up-regulated 1.5 fold. A selection of other genes associated with neurogenesis that were up- or down-regulated is listed in Table I. Concomitant with the increased expression of markers indicative of neurogenesis (Table I), there was a decrease in expression of genes associated with hematopoiesis (Table II). The greatest changes occurred in the expression of HLA class I locus C heavy chain, macrophage receptor MARCO, secreted T cell activation protein Attractin (attractin), leucocyte iminunoglobulin-like reveptor-8 (LIR-8), thymocyte antigen CD1c, erythropoietin receptor and erythropoietin.

Figure 1B:
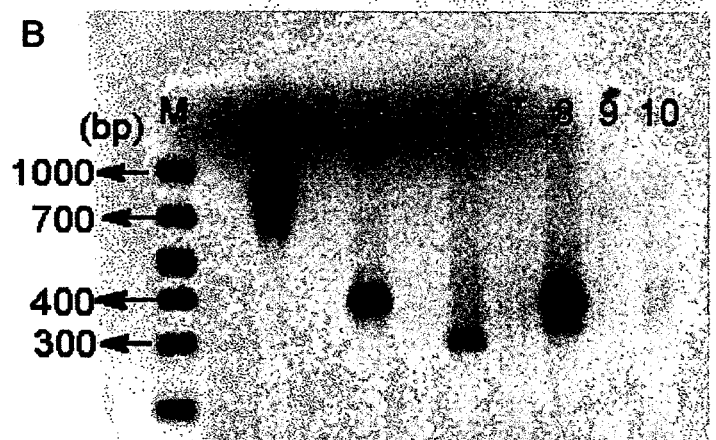
Figure 1C:
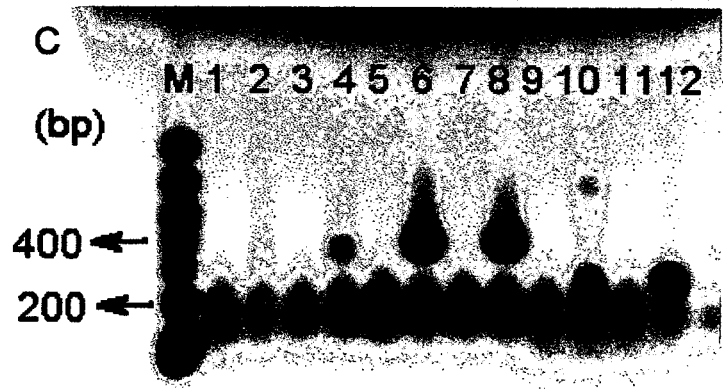

In a parallel set of experiments, total RNA was extracted, and RT-PCR was performed. The mRNA for nestin and necdin was identified in both control and RA+NGF treated cultures using primers based on published human sequences. In each case a product of appropriate length was seen on the gel (FIG. 1A for untreated cells and FIG. 1B for treated cells). Nestin is considered a marker of early neural development, but can also be seen in endothelial precursors. Necdin is the gene that codes for neuron specific nuclear protein. The m-RNA for Musashi-1, the earliest marker of neural precursors was detected in RA+NGF treated cultures and minimally detected in DMEM-treated controls. The mRNA for neurite outgrowth promoting protein (pleiotrophin) was detected in RA+NGF treated cells, but the signal was much weaker in untreated cultures (FIG. 1C). The mRNA for glypican-4 was detected under both conditions. The mRNA for GFAP, a marker of astroglial cells, was also detected under both conditions, though the signal was stronger in the RA+NGF treated cells. No messenger RNA for neurofilament subunit NF-L was detected in either treated or untreated cells although it was seen to be up-regulated in the microarray. A negative RT control (without reverse transcriptase) was run with all the reactions to check for genomic DNA contamination in the RNA preparation while human-actin primers (Clontech) were used as a positive control. We also tested primers for Musashi-1 and Neurofilament subunit NF-L using human brain RNA (Clontech) by RT-PCR; these each generated a single band of appropriate length (data not shown).

Figures 2A, 2B, 2C, 2D, 2E:
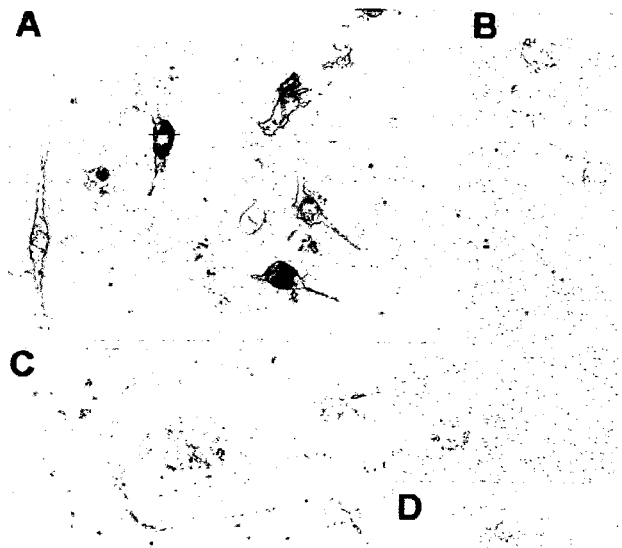
FIG. 2 is representative of microscopic examination of immunostained cultures of cells which are tested for immunoreactivity with antibodies to neuronal markers. Certain of the figures evidence that the cells were immunoreactive with Mushashi-1 (FIG. 2A), β-tubulin III (FIG. 2B) and GFAP, a marker of astrocytes, (FIG. 2E).

Microscopic examination of immunostained cultures treated with RA+NGF revealed a heterogeneous mixture of cell types ranging from large flat epithelioid cells to small spindle-shaped cells with fine branching neuritic processes. A significant proportion (5–10%) of the small cells in the RA+NGF treated cultures, but not control cultures treated with DMEM, were Musashi-1 immunoreactive (See FIG. 2A). A similar proportion (5%) of the small cells exhibited β-tubulin III immunoreactivity (FIG. 2B). Approximately 50% of the cells were immunoreactive for BrdU, indicating that the cells were continuing to proliferate (data not shown). Antibodies to nestin (purchased from Chemicon, raised against rat nestin) failed to recognize the human form of nestin, though they had been shown to react with rat nestin in rat bone marrow-derived neural progenitor cells (Sanchez-Ramos, et al., *Neuroscience News* 3, 32–43, 2000). Approximately 50% of RA+NGF treated cells were immunoreactive for GFAP, a marker of astrocytes (FIG. 2E). Western blots of the cultures confirmed the presence of Musashi-1 protein, β-tubulin-III protein, pleiotrophin GFAP and NeuN in both treated and untreated cells. Densitometric analysis of the blots showed that NGF+RA treatment increased protein expression (relative to β-actin) of Musashi-1, β-tubulin-III, pleiotrophin and NeuN (Table III).

TABLE I

Expression of Genes Associated with Neurogenesis

| Gene transcript | Fold change following RA + NGF | |
|---|---|---|
| Neurite outgrowth-promoting protein | +44 | extracellular matrix-associated protein that enhances axonal growth in perinatal cerebral neurons [Raulo, 1992 #384] |
| Glypican-4 | +4.9 | glypican-4 is expressed in cells immunoreactive for nestin and the D1.1 antigen, markers of neural precursor cells. Glypican-4 expression not detected in early postmitotic or fully differentiated neurons [Hagihara, 2000 #375] |
| β-tubulin folding cofactor D | ~+4.6 | |
| Pro-galanin | +3.9 | Found in neurons of arcuate nucleus of hypothalamus |
| FE65 stat-like protein | ~+3.8 | the exon 9-inclusive (E9) form is exclusively expressed in neurons [Hu, 1999 #369] |
| Glial acidic fibrillary protein | ~+3.2 | |
| Neuron derived orphan receptor | ~+2.2 | |
| Neuronal pentraxin II (NPTX2) | ~+2.3 | member of a new family of proteins identified through interaction with a presynaptic snake venom toxin taipoxin; may function during synapse formation and remodeling [Kirkpatrick, 2000 #393] |
| Neuronal growth protein 43 (GAP-43) | ~+2.7 | Identifies neurons, but also developing muscle cells [Moos, 1993 #395] |
| Neuronal PAS1 (NPAS1) | +2.3 | transcription factors selectively expressed in the central nervous system [Zhou, 1997 #394] |
| Neuronal DHP-sensitive, voltage-dependent, calcium channel alpha-1D subunit | +2.1 | |
| Bone morphogenetic protein 1 (BMP-1) | +2 | BMP-1/Tolloid is found at the neural plate/ectodermal transition. Expression is maintained in the premigratory neural crest, and transiently in the migrating cephalic neural crest cells. [Marti, 2000 #391] |
| Retinal glutamate transporter EAAT5 | ~+2 | |
| TrkC | ~+2 | Receptor for neurotrophin-3 (NT3) |
| ENO2 gene for neuron specific (gamma) enolase | +1.9 | |
| Human brain protein recognized by the sera of patients with paraneoplastic sensory neuronopathy | ~+1.8 | |
| Bone morphogenetic protein 2A | ~+1.8 | |
| Neuronal PAS2 (NPAS2) | +1.7 | transcription factors selectively expressed in the central nervous system [Zhou, 1997 #394] |
| Survival motor neuron pseudogene | +1.7 | |
| Glial Growth Factor 2 | +1.6 | |
| Neural cell adhesion molecule (N-CAM) Exon SEC | ~+1.6 | |
| Follistatin-related protein (FRP) | +1.6 | |
| Microtubule-associated protein 2 (MAP2) | ~1.6 | |
| Vesicular acetylcholine transporter | +1.6 | |
| Neurofilament subunit M (NF-M) | +1.5 | |
| Neurofilament subunit NF-L | +1.5 | |
| Musashi1 | ~1.5 | |
| Bone morphogenetic protein 11 (BMP11) | +1.5 | BMP-11 is expressed in the developing nervous system; at higher doses induces nervous tissue [Garner, 1999 #392] |
| Tenascin-C | −8.8 | Tenascin-C is an extracellular matrix protein that inhibits neurite extension, and promotes cell proliferation and migration [Thomas, 1996 #397; Anstrom, 1996 #398] |

Table II

Downregulation of Genes Associated with Development of Blood Lines

| | Fold decrease |
|---|---|
| HLA class I locus C heavy chain | −6.4 |
| Macrophage receptor MARCO | −4.9 |
| secreted T cell activation protein Attractin (attractin) | −3.6 |
| alpha-1 collagen type II | −3.0 |
| Leucocyte immunoglobulin-like receptor-8 (LIR-8) | −2.8 |
| Thymocyte antigen CD1c | −2.5 |
| Erythropoietin receptor | ~−2.6 |
| Erythropoietin | ~−2.4 |
| Monocyte chemotactic protein-2 | −2.2 |
| LAG-3 mRNA for CD4-related protein involved in lymphocyte activation | ~−2.3 |
| Interleukin-7 receptor (IL-7) | −2.2 |
| Complement receptor type 1 | −2.1 |
| T cell receptor | −2 |
| p50-NF-kappa B homolog | −2 |
| Lymphocyte-specific protein tyrosine kinase (LCK) | ~−2 |
| LAG-3 mRNA for CD4-related protein involved in lymphocyte activation | ~−2.3 |
| Erythrocyte membrane protein Rh30A (Rhesus antigen) | ~−2.1 |
| Erythrocyte membrane protein band 4.2 (EPB42) | ~−2.9 |
| Leukocyte IgG receptor (Fc-gamma-R) | −1.8 |
| Erythroblast macrophage protein EMP | −1.5 |

TABLE III

Densitometric Measurement of Expressed Proteins Separated by Western Blot

| Protein | MW marker | Ratio to β-Actin DMEM | Ratio to β-Actin NGF | % change |
|---|---|---|---|---|
| Musashi-1 | 36 kD | 0.805 | 0.93 | +15.5% |
| β-III tubulin | 75–80 kD | 0.328 | 0.50 | +52.4% |
| Pleiotrophin | 18 kD | 0.179 | 0.315 | +75.9% |
| GFAP | 46 kD | 0.538 | 0.515 | −4.3% |
| NeuN | 51 kD | 0.6 | 0.715 | +19.1% |
| β-Actin | 42 kD | | | |

Discussion of Results

These findings demonstrate that human umbilical cord blood contains cells that can be induced to express markers of neural development, including Mushashi-1, glypican-4 and β-tubulin III. Recent work has demonstrated Musashi-1 immunoreactivity in the developing and/or adult CNS tissues of frogs, birds, rodents, and humans (Kaneko, et al., *Developmental Neuroscience* 22, 139–53 (2000). The anti-Musashi-1 monoclonal antibody has been shown to react with undifferentiated, proliferative cells of the sub-ventricular zone in the CNS of all vertebrates tested. Glypican-4, upregulated five-fold in the cord blood cultures treated with RA+NGF, has been reported to be expressed in cells immunoreactive for nestin and the D1.1 antigen, other known markers of neural precursor cells, but it has not been detected in early postmitotic or fully differentiated neurons (Hagihara, et al, *Developmental Dynamics* 219, 353–67 (2000). β-tubulin III is one of the most specialized tubulins specific for neurons (Fanarraga, et al., *European Journal of Neuroscience* 11, 517–27 (1999). Both the upregulation and the post-translational processing of class-III beta-tubulin are believed to be essential throughout neuronal differentiation (Laferriere, et al., *Cell Motility & the Cytoskeleton* 35, 188–99 (1996) and Laferriere, et al., *Biochemistry & Cell Biology* 75, 103–17 (1997).

The cord blood cultures treated with RA+NGF also increased expression of many genes specific for neurons including pentraxin II, GAP43, FE65 stat-like protein, neuronal PAS1 and PAS2. Neuronal pentraxin II is a member of a new family of proteins identified through interaction with a presynaptic snake venom toxin taipoxin. Neuronal-pentraxin-II may function during synapse formation and remodeling (Kirkpatrick, et al, *Journal of Biological Chemistry* 275, 17786–92 (2000). Neuronal growth associated protein 43 (GAP43) is considered a specific neuronal marker but may also be expressed in developing myocytes (Moos, T. & Christensen, L. R. GAP43 identifies developing muscle cells in human embryos. *Neuroreport* 4, 1299–302 (1993). FE65 stat-like protein (the exon 9-inclusive form) is specifically expressed in neurons (Hu, et al., *Journal of Neuroscience Research* 58, 632–40 (1999). Neuronal PAS1 and PAS2 are transcription factors selectively expressed in the central nervous system (Zhou, et al., *Proceedings of the National Academy of Sciences of the United States of America* 94, 713–8 (1997). Other genes indicative of neurogenesis that were expressed following treatment included the neurofilament subunits-NF-L and NF-M, microtubule associated protein 2 (MAP2), the vesicular acetyl choline transporter, and neuronal DHP-sensitive, voltage-dependent, calcium channel alpha-1D subunit. Cord blood cells expressed mRNA for neuronal specific enolase, but this protein is also expressed by many cells in bone marrow, especially megakaryocytes. The greatest change observed in cord blood cultures treated with RA+NGF was a 44 fold increase in expression of mRNA for an extracellular matrix-associated protein that enhances axonal growth in perinatal cerebral neurons (Raulo, et al., *Journal of Biological Chemistry* 267, 11408–16 (1992). At the same time there was a significant decrease in expression of mRNA for tenascin, an extracellular matrix protein which inhibits neurite outgrowth (Kukekov, et al., *Experimental Neurology* 156, 333–44 (1999). There was also evidence for glial cell development. Increased expression of the glial cell marker GFAP was measured in the microchip data, and confirmed by immunocytochemistry. Concomitant with the increased expression of markers indicative of neurogenesis, there was a decrease in expression of genes associated with development of blood cell lines.

The present findings provide evidence that cord blood contains a multi-potent cell capable of differentiating into a neural lineage. The ease with which the umbilical cord blood can be obtained, stored, and expanded in culture could make this a preferable source of cells for transplantation for neurodegenerative diseases, gene delivery to the central nervous system, and repair of brain and spinal cord injuries.

Example

Identification and Isolation of Mononuclear Cells Expressing Neuronal, Astrocytic or Oligodendrocytic Markers and Use of Mononuclear Cells to Effect Transplantation in Stroke This series of experiments is directed to using both cell culture techniques and an animal model of cerebral ischemia to establish human cord blood as a viable source of NSCs for the treatment of CNS disease or injury. These studies determine the existence of mononuclear cells in cord blood that express neuronal, astrocytic or oligodendrocytic markers and identify those mononuclear cells that give rise to neural cell lineages. The cord blood stem cells are shown to provide a stable, readily available source of NSCs which become functional neurons and are capable of producing behavioral recovery at a comparable level to that observed with transplantation of fetal neurons.

General Methods.

Culture Media. The frozen cells are thawed, spun down and resuspended and plated in 75 mm culture flasks in minimal essential medium (DMEM) supplemented with 2 mM glutamine(100× stock from Gibco/BRL), 0.001% B-mercaptoethanol, 1× non-essential amino acids (100× stock from Gibco/BRL) and 10% FBS (stem cell qualified, Gibco/BRL). After 24 to 72 hrs, the medium is replaced with serum free "Neural Proliferation Medium" which consists of N2 medium (DMEM/F12 1:1, Gibco/BRL) supplemented with 0.6% glucose, insulin 25 ug/ml, transferrin 100 ug/ml, progesterone 20 nM, putrescine 60 uM, selenium chloride 30 nM, glutamine 2 mM, sodium bicarbonate 3 mM, HEPES 5 mM, heparin 2 ug/ml and EGF 20 ng/ml, bFGF 20 ng/ml. Differentiation medium consists of the "Neural Proliferation Medium" without the EGF and bFGF, but instead containing retinoic acid (0.5 μM) plus a specific growth factor (NGF, BDNF, or GDNF)

Transfection of Cord Blood Cells with Fluorescent Green Protein Driven by the Musashi-1 Promoter.

An ΔE1 adenovirus bearing hGFP under the control of the Mushashi-1 promoter (AdP/Musashi) (generously donated by H. Okano of Japan) are used to transfect umbilical cord blood cells. This adenoviral DNA vector is a plasmid DNA that contains a portion of the viral genome in which the E1 A region is deleted and the hGFP under control of the-Musashi-1 promoter has been inserted in the place of the E1A region of the genome. Cells to be transfected are plated in 0.5 ml of serum-free "Neural Proliferation Medium". To each culture dish of cells to be transfected 0.8 μg of the DNA is diluted and mixed into 50 μl of Opti-Mem® I Reduced Serum Medium Without Serum (Life Technologies, Inc). Eight μl of Plus Reagent Mix is added and incubated at room temperature for 15 min. Lipofectin Reagent (Life Tech, Inc) is diluted and mixed in a second tube (0.5 μl into 50 μl of Opti-Mem I Reduced Serum Medium Without Serum). After 30 min incubation at room temperature, the precomplexed DNA is mixed with diluted Lipofectin Reagent and incubated for 15 min at room temperature. Then the DNAPlus-Lipofectin Reagent complexes (100 μl) are added to each well and mixed gently by rocking the plate back and forth. The cultures are incubated at 37° C. in 5% CO2 for 4–5 h. After 24 to 48 hrs, selected cultures are harvested to assess efficiency of transfection.

Isolation of RNA. Total RNA is isolated from human cord blood cells (or fractions thereof) using the RNA STAT-60 kit using the protocol recommended by the manufacturer (Tel-Test "B", Inc. Friendswood, Tex. 77546). Following RNA isolation, its OD densityis measured at 260 nm, and stored at −80° C. Integrityis tested on 1% non-denaturing Seakem LE agarose gel (FMC Bioproducts, Rockland, Me.).

Reverse Transcription (RT). RTis performed using random hexamers as primers. Final volumeis 20 μl with 1 μg of total RNA from each fraction of cells. The reaction mixture contains 1 mM of each deoxynucleoside triphosphate (dNTP), 1 U/μl RNase inhibitor, 5 mM MgCl$_2$, 2.5 U/μl Murine leukemia virus (MuL V) reverse transcriptase, 2.5 μM random hexamers in 50 mM KCl and 10 mM Tris-HCl (pH 8.3). It will first be incubated at room temperature for 10 min, and then at 42° C. for 15 minutes. The mixture will then be heated at 99° C. for 5 minutes and cooled on ice for 5 min to inactivate the transcriptase.

Polymerase Chain Reaction (PCR). PCRis performed in the same tubes as RT, in 100 μl total volume. Final concentrations are 2 mM MgCl$_2$, 0.2 mM of each dNTP, and 2.5 U/100 μl Ampli Taq DNA polymerase in the 50 mM KCl and 10 mM Tris-HCl buffer (pH 8.3). For generation of various cDNA fragments, a PE 9700 thermocycler (Perkin Elmer, Foster City, Calif.)is programmed as follows: 1 cycle at 95° C. for 105 sec, 35 cycles at 95° C. for 15 sec, followed by 60° C. for 30 sec, and finally 1 cycle at 72° C. for 7 min. Both RT and PCR are done using Perkin Elmer's GeneAmp RNA PCR kit. To identify the presence of various neuronal markers, primers are constructed based on published human sequences. For Nestin (accession #X65964), forward primer: nt 2524–2542 and reverse primer: nt 2921–2903. For Musashi-1 (accession #AB012851), forward primer: nt 319–339 and reverse primer: nt 618–598. For Necdin (accession #AB007828), forward primer: nt 2374–2393 and reverse primer: nt 2767–2747. For Neurofilament subunit NF-L (accession #X05608), forward primer: nt 3155–3173 and reverse primer: nt 3521–3501. Primers were selected using the SEQWEB (version 1.1) software available on the USF computer network.

Western Blot. Cultures are washed three times in cold phosphate buffered saline (PBS), scraped into ice-cold PBS, and lysed in ice-cold lysis buffer containing 20 nM Tris/HCl (pH=8.0), 0.2 mM EDTA, 3% Nonidet P-40, 2 mM orthovanadate, 50 mM NaF, 10 mM sodium pyrophosphate, 100 mM NaCl, and 10 μg each of aprotinin and leupeptin per ml. After incubation on ice for 10 min, the samples are centrifuged at 14,000×g for 15 min and supernatants are collected. An aliquotis removed for total protein estimation (Bio-Rad assay). An aliquot corresponding to 10 μg of total protein of each sample is separated by SDS/PAGE (10%) under reducing conditions and transferred electrophoretically to nitrocellulose filters. Nonspecific binding of antibodyis blocked with 5% non-fat dry milk overnight at 4 C.

MCAO Induction. Sprague Dawley rats are anesthetized with Isofluorane and an incision made from the caudal end of the sternomastoid and sternothyroid muscles extending toward the ears. Using blunt dissection techniques, the right common carotid artery is exposed and carefully dissected free of the vagus nerve. The external carotid will then be tied off and an embolus (a 40 cm length of 4.0 monofilament)is inserted through the external carotid approximately 25 mm into the internal carotid. At this point, the embolus is blocking the origin of the right middle cerebral artery. The embolus is left in place for 1 hr. After removal, the external carotid is cauterized and the incision closed. The animals are allowed to recover for 24 hr prior to transplantation.

Transplantation. The freshly isolated MNCs are resuspended in HBSS+15 mM HEPES at a cell concentration of 100,000 cells/μl. The coordinates for the injection site are 1.2 mm anterior and +2.7 mm lateral to the bregma and −5.2 and −4.7 mm ventral to the dura with the toothbar set at zero. Five microliters of the cell suspension are deposited at 2 sites in the striatum adjacent to the infarct site along a single needle tract. Each injection of 2.5 μlis delivered at the rate of 1 μl/min. The needle is left in place for an additional 5 min after the injection and then withdrawn slowly. The incisionis closed with wound clips. For the transplantation of the expanded and/or differentiated MNCs, the cells are lifted from the culture flasks with gentle mechanical trituration or lifted with trypsin (0.25%) and 1 mM EDTA at 37 C. for 3–4 min and washed three times with HBSS+15 mM HEPES. Cell concentrationis adjusted to 100,000 cells/μl.

Behavioral testing methods. Twenty-four hours after stroke, the animals undergo a standardized neurological screening exam measuring 5 motor and postural activities to verify the extent of the MCAO damage. This battery is repeated at one month post stroke. In addition, the animals are tested at both time points in the Passive Avoidance test of learning and memory. In the acquisition phase of the test, the animal is placed on a platform in the corner of a Plexiglas cage. When it steps off the platform, the rat will receive a scrambled foot shock (approximately 2 mA) for as long as it remains off the platform. Learning is measured by the amount of time required for the rat to remain on the platform continuously for 3 minutes, and the number of times it leaves the platform. Twenty-four hours later, retention is measured by placing the rat on the platform, and recording the latency to step-down measured to a maximum of 3 min and the number of step-downs. Animals are also tested in the Rotorod Test of motor coordination. The animal is placed on a revolving rod (16 rpm) and the latency to the first fall as well as the number of falls in a 3 minute test is recorded. The test is repeated twice for a total of 3 tests per testing session with a minimum 30 min. rest between tests. The third behavioral observation includes Spontaneous Activity Monitoring. The animals are placed in a square acrylic box overnight with an infrared grid to measure movement and direction. The Elevated Body Swing Test, a measure of motor asymmetry is also performed. The animal is held by the base of the tail and lifted 2" above the base of the cage. The direction that the head and body is lifted is recorded. The test is repeated 20 times. The final test is Skilled Forepaw Use. This is also a measure of motor asymmetry. The animal is placed in an acrylic chamber with two descending staircases. Each step is baited with 5 food pellets. The chamber is designed such that each staircase can only be reached by one paw. The number of pellets retrieved measures the function of each limb. There is a 5 day training period, during which the animals are partially food deprived. All behavioral data are reported as mean±sem.

Tissue Preparation in Culture Preparations. After 7–14 DIV, the cultures are fixed with 4% paraformaldehyde in 0.1 M phosphate buffer (PB) for 20 minutes. The cultures are then washed 3 times with phosphate buffered saline prior to beginning immunocytochemistry.

Tissue Preparation of Brain Sections. The rats are sacrificed under deep chloral hydrate (10%) anesthesia and transcardial perfusion of the brain with 50 ml of 0.1 M phosphate buffer (PB) and then 250 ml 4% paraformaldehyde in 0.1 M PB performed. The brain is removed, post-fixed for 24 hr and cryopreserved in 20% sucrose prior to cutting 30 μm thick frozen sections through the forebrain.

Immunohistochemistry. Single and double immunofluorescence histochemistry are performed. Briefly, the floating sections will first be quenched by incubation in a 10% methanol, 3% hydrogen peroxide solution in phosphate buffered saline (PBS) followed by pre-incubation in 10% normal serum (horse or goat; Vector) in 0.3% Triton-X100 (Sigma) in PBS. The sections are transferred to primary antibody in 2% normal serum, 0.3% Triton X-100/PBS and incubated overnight at 4° C. The primary antibodies that are used include: Musashi-1 (donated by Prof. H. Okano), Nestin (1:200, Chemi-Con); vimentin (1:500 Chemi-Con) as markers of early neural precursors; NeuN (1:100, Chemi-Con) and Hu (1:20 Molecular Probes) class III β-tubulin (1:200, Sigma) to identify human neurons at specific stages of development; human specific GFAP (1:200, Sternberger Monoclonals) to identify astrocytes; and O4 or 2'3' cyclic nucleotide 3' phosphodiesterase (CNPase, 1:200, Sigma) to identify oligodendrocytes derived from the transplanted human MNCs. The sections are then washed in PBS before being placed in secondary antibody conjugated to either fluorescein or rhodamine for 2 hours. The sections are rinsed in PBS, mounted and coverslipped with Vectashield. Confirmation that a cell is doubly-stained with be obtained by z-stacking analysis of images collected with a Zeiss Confocal Microscopes (LSM 510).

Cell Counts. For assessment of cell number in culture, 20 random visual fields (40× objective) in 4 culture dishes for each marker in 3 replicates are viewed. The total number of cells and the number of positively labeled cells are counted. For each experimental condition, the number of positive cells and the total number of cell nuclei stained with 4', 6-dimidinee-2'-phenylindole dihydrochloride (DAPI) are determined. The total counts are then expressed as a percentage of the total DAPI-stained nuclei. For quantification of immunofluorescence in brain sections, an unbiased counting methodology are used. Neurons are directly counted in a small number of sections at predetermined uniform intervals for the entire set of sections containing specific CNS nuclei. Within each section to be counted the field of view is focused at the top of the section using a 40× objective. The focus is then shifted through the section and the number of positive profiles not present at the top of the section is counted.

Analysis. The number of animals to be used in these studies was based on a power analysis of data obtained in previous experiments in this laboratory. The analysis showed that a minimum of 10 animals per group is needed to find a difference in the variables of interest at a significance level of $p<0.05$. All quantifiable results are expressed as mean±sem and are analyzed using Analysis of Variance (ANOVA). All post-hoc tests are conducted using a Scheffé test.

Identification and Isolation of Stem/Progenitor Cells Present in Umbilical Cord Blood The ideal way to identify and isolate neural progenitor cells among the heterogeneous population of mononuclear cord blood cells is to utilize a cell surface marker to which a fluorescent or magnetic bead antibody tag is attached to facilitate sorting and separation.

Unfortunately, both Nestin and Musashi-1 are located in the cytoplasm. Surface-based immunoselection strategies do not yet permit the prospective identification or specific extraction of neural stem/progenitor cells. A novel strategy has been used to identify and monitor internal molecular markers of neural progenitor cells and to separate the neural progenitors from other cells using fluorescence activated cell sorting (FACS) (N. S. Roy et al., *Journal of Neuroscience Research* 59, 321–31 (2000)). This method relies on coupling the promoters required for neuroepithelial-specific gene expression with a reporter gene (either lacZ or Green Fluorescent Protein-GFP). More specifically, cis-regulatory elements (the "promoter") required for the expression of Musashi-1 or α-tubulin-1 were placed upstream to the reporter gene GFP (Wang et al., *Nature Biotechnology* 16, 196–201 (1998) and N. S. Roy et al., *Journal of Neuroscience Research* 59, 321–31 (2000)) Using this approach, neural progenitors and young neurons have been identified and selectively harvested from a variety of heterogeneous samples, including both adult and fetal mammalian forebrains at different developmental stages (Wang, et al., supra, and Keyoung et al., *Society for Neuroscience Abstract*, 159 (2000)).

Experimental Design. We identify and separate neural progenitor cells by FACS of cord blood cells transfected with the gene for GFP, driven by the neuronal promoter α-tubulin-1 (Tα1) or by the Mushashi-1 promoter. Mononuclear cells are obtained from the placental stump of the umbilical cord after delivery and processed by Ficoll centrifugation (See General Methods). This results in nearly 100% recovery of mononuclear cells. These cells are cryopreserved in aliquots of 2 million cells until they are to be used. After thawing, and plating in culture flasks in supplemented minimal essential medium (DMEM) plus FBS 10% for 48 hrs, the medium is changed to "Neural Progenitor Proliferation Medium" for 2 days (See Methods for definition of the media). Then, the mononuclear cells are transfected in a suspension culture with a plasmid or viral vector containing the gene for GFP under the control of P/Tα1 or Musashi-1 (See General Methods for details on Transfection technique and description of the vectors). After a 6-hour transfection, the cells are spun down, resuspended in "Neural Progenitor Proliferation Medium" and plated in small culture flasks (See General Methods). GFP should typically be expressed by appropriate target cells within 2 days of transfection. Flow cytometry and sorting of GFP+ cells are performed after 2–7 days in culture. Cells are washed, dissociated and analyzed by light forward and right-angle (side) scatter, and for GFP fluorescence through a 510±20 nm band pass filter as they traverse the beam of the Laser (488 nm, 100 mW). Sorting is done using a purification-mode algorithm. Cells detected as being more fluorescent than background are sorted at 1,00–3,000 cells/s. Sorted GFP+ cells are plated in 24 well culture plates in "Neural Proliferation Medium" (See General Methods for details) and BrdU. At 2 and 7 days post-FACS, the sorted cultures are fixed and immunostained for BrdU together with either Mushashi-1, β-tubulin-III, Nestin, NeuN, MAP2, glial fibrillary acidic protein (GFAP) or O4 (to detect oligodendrocytes).

Results and Alternative Method for Enriching Stem-like Cells. Cells transfected with the plasmid DNA encoding P/Tα1:GFP or the viral vector encoding P/Musashi:GFP identify neural progenitors and immature neurons as evidenced by immunoreactivity for Mushashi-1, β-tubulin-III, and Nestin. In most instances, at least 50% of the Mushashi-1(+) cells are co-labeled with BrdU antibody indicating that the cells are proliferating. Based on the work of Wang et al., supra, many Musashi1-driven GFP+ cells should be labeled for up to 7 to 10 days. These neural progenitors and their daughters should be selected and substantially enriched by FACS. Further, they also showed that 0.36% of adult ventricular zone dissociates expressed Tα1-driven GFP. Assuming that only 0.01% of cord blood cells express Mushashi1-driven GFP, and the transfection efficiency using the plasmid DNA is 12.5%, we estimate that for every $5 \times 10^6$ cord blood cells processed, we shall obtain 625–1000 neural precursor cells. However, using an adenoviral vector results in a much greater transfection efficiency. For that reason we also use a ΔE1 adenovirus bearing hGFP under the control of the Musashi promoter (AdP/Musashi:hGFP) provided generously by H. Okano of Japan.

In an alternative method, we first identify the least committed stem-like cells from the mononuclear cells in the cord blood and isolate this population from both CD34+ and CD34− cells prior to inducing proliferation and promoter-based isolation of neural progenitors. The basic premise of this strategy is that stem cells are quiescent and express very few cell surface markers, except during a proliferation phase. Primitive stem cells fail to stain with Hoescht 33342 and Pyronin Y and can be separated on this basis using FACS. Further, separation of cells that express P-gp, the transmembrane protein product of the multiple drug resistance gene (MDR), which is likely to be expressed in cells that exhibit characteristics of stem cells, could also be performed. These staining characteristics could be used to separate stem cells from cord blood mononuclear cells using FACS. If FACS demonstrates that P-gp+ cells are also cells that fail to stain with the fluorescent dyes (Hoescht 33342 and Pyronin Y), then magnetic bead cell sorting are used to physically separate the P-gp immunoreactive cells from cord blood. In order to increase the yield of neural progenitor cells, it is preferable to start with the smaller population of the least committed cells found in cord blood.

Assessing the Self-Renewal Capacity of the Neural Progenitor Population

In the example above, we identifiy a subpopulation of cells enriched with neural progenitor cells or uncommitted stem cells. It will, therefore, be critical to expand the cell populations in order to obtain sufficient cells for study and eventually for transplantation. In this study we will determine whether there are differences in the ability of the isolated populations of cells to proliferate and the best agents for inducing proliferation in the neural progenitors.

Experimental Design. Mononuclear cells are obtained and the subpopulations isolated as described above. We will focus primarily on the GFP+ cells containing neural progenitors. These cells are plated in Corning T75 flasks with "Neural Progenitor Proliferation Medium". This serum-free, defined medium contains epidermal growth factor (EGF) and basic fibroblast growth factor (bFGF) and is used to induce proliferation of neural stem cells derived from fetal or adult brains. Once the cultures reach confluence (about 1 week), the cells are lifted by incubation with 0.25% trypsin, and 1 mM EDTA for 3–4 minutes. An aliquot of cells is replated with BrdU to assess the proportion of cells that are actively proliferating. The cells are replated after 1:3 dilution with Neural Progenitor Proliferation medium. Cell yield and viability is also determined with the trypan blue dye exclusion assay after each passage, for at least five passages.

Results. Neural stem cells proliferate with exposure to EGF or bFGF and the combination of these growth factors optimally allow for the continuous, rapid expansion and passaging of human neural stem cells. Alternatively, there is an extensive list of trophic factors and cytokines that may be more or less effective in inducing proliferation. These include other members of the EGF family such as transforming growth factor (TGF)-, amphiregulin, betacellulin and heregulin; FGF2 and the related FGF1 and FGF4, platelet-derived growth factor family (PDGF), interleukins, and members of the TGF β superfamily. There may be some degree of differentiation that occurs despite culturing in presence of known mitogens. The proportion of cells that continue to proliferate (determined by the BrdU assay before each passage) will guide us in the selection of the optimal mitogens for the neural progenitors.

Assessing the Capacity of Cord Blood Derived Neural Progenitors to Differentiate into Meurons, Astrocytes or Oligodendrocytes In Vitro.

The mononuclear cells which proliferate subpopulations of mononuclear cells as established above can differentiate into neurons, astrocytes and oligodendrocytes. We have shown that a small population of non-hematopoietic stem cells in the bone marrow stromal cell fraction will differentiate into neurons and astrocytes. Moreover, preliminary results show that cord blood treated with RA+NGF for less than one week express a marker seen in early neuronal development, β-tubulin-III. In this study, we demonstrate that treatment with "Differentiation Media" will drive our neural progenitors into neuronal and glial phenotypes.

Experimental Design. Mononuclear cells from the first or second passage of the subpopulations with the greatest proliferative capacity as determined above (GFP+ cells) are replated in 35 mm culture dishes in the presence of a "neuronal differentiation medium" (See Methods for definition) and a series of specific neurotrophic factors. The first to be tried are brain derived neurotrophic factor (BDNF, 10 ng/ml) since this media has been used previously with bone marrow stromal cells to differentiate the cells along neural lineages. After 7–14 days in vitro (DIV), cultures are processed for Western blotting, RT-PCR and immunocytochemistry to identify cells that express neural markers. The markers to be examined include nestin, vimentin, glial fibrillary acidic protein (GFAP) to label astrocytes, O4, myelin basic protein and CNPase to identify oligodendrocytes and NeuN, β-tubulin class III, Hu, Neuron-Specific Nuclear antigen (NeuN), human specific neurofilament and microtubule associated protein (MAP-2) to identify neurons. Quantification is described in the General Methods.

Results. Neural markers are observed in the subpopulations chosen for assay based on preliminary results with cord blood and results obtained with differentiation of bone marrow stromal cells. Further, the population most likely to give rise to these neural cells is the GFP-expressing cells (driven by the Musashi-1 promoter). Alternatively, it may be necessary to use the stem-like cells obtained by selecting the least committed of cells from the cord blood, nonetheless we are still able to obtain significant numbers of differentiated neurons and glia following treatment with differentiation media.

Example

Expanded Population of Mononuclear Cells and Expression of Neural Markers After Transplantation into Middle Cerebral Artery Occlusion (MCAO) Model of Stroke In addition to demonstrating the existence of the neural phenotype in vitro, it is important to show that the isolated and differentiated cells could express or maintain their neural phenotype after transplantation. The culture environment is easily controlled and manipulated. The environment into which the cells are transplanted in vivo is much less predictable; and there are many influences on the cells once they are placed in situ, some of which may alter the proliferative capacity or phenotypic lineage of the cell. Therefore, we demonstrate that these stem-like cells maintain the ability to become neurons, astrocytes or oligodendrocytes in the brain.

Experimental Design. Sprague Dawley rats (n=10/group) are assigned to one of the following groups: 1) Middle cerebral artery occlusion (MCAO); 2) MCAO with a striatal transplant of freshly isolated mononuclear cells; 3) and 4) MCAO+ expanded GFP+ cells from the two subpopulations with the highest proliferative capacity as determined above; 5) and 6) MCAO+ expanded/minimally differentiated GFP+ cells as determined above. The untreated cord blood cells in group 2 are labeled with the fluorescent dye PKH26 for later identification in the brain and then transplanted into the striatum in the penumbral region of the infarct. (The isolated neural progenitors will already be labeled by the GFP). The animals are evaluated on a series of behavioral measures and a neurological exam at 24 hr and one month. This includes two paradigms we have used to demonstrate behavioral deficits after stroke and recovery following transplantation, the passive avoidance test of cognitive function and the rotorod test of motor coordination. The animals will then be perfused with 4% paraformaldehyde and the brains harvested for histological and immunohistochemical analysis of graft survival and neural differentiation. Sections are examined for the presence of PKH26-positive (or GFP+) cells, and cells that express human Nuclear Matrix Antigen (NuMA), allowing a second method of identifying human cord blood-derived cells in the rat brain). Other sections are double-labeled for PKH26 or NuMA and Hu, class III β-tubulin, NeuN, GFAP, O4. The proportion (%) of cord blood derived cells (NuMA-ir and PKH26+) that express neuronal markers (NeuN, Hu, or class III β-tubulin), glial markers (GFAP) and oligodendrocyte markers (O4) are determined.

Results. Based on our preliminary results we see both behavioral improvements and surviving stem-cell progeny in the MCAO-injured brain. Behavioral improvements are observed in all transplant groups, although it is better in the expanded/minimally differentiated cells where the expanded cell population have already been committed to a neural lineage and therefore may be expected to express more neurons. With the whole MNC cell fraction, there are fewer of the subpopulation cells that give rise to neural cells than in the expanded subpopulations.

Example

Effect of Transplanation of Human Umbilical Cord Mononuclear Cells in Stroke

In a small series of pilot studies, the cord blood mononuclear cells were transplanted into the striatum of animals that had either undergone a permanent or temporary (1 hr) middle cerebral artery occlusion (MCAO). The cells (500, 000 cells/implant) were transplanted immediately upon thawing or were treated in culture for a week with various trophic factors (BDNF, NGF, EGF+bFGF) prior to transplantation. Preliminary results obtained from the temporary stroke model revealed differences between the groups on the rotorod test of motor coordination. Animals which received the retinoic acid+NGF treated mononuclear cells were able to stay on a rotating axle longer and fell off fewer times in the 3 minute test period than did all other animals in the study. This study evidenced that the umbilical blood cells provide a novel cell source for transplantation in stroke which can improve function.

Example

Parenteral Administration of Cord Blood Fractions in the Treatment of Neurological Damage from Ischemia (Stroke)

Methods and Materials
1. HUCB Sources and Preparation:
HUCB was provided and analyzed by Cryocell international, INC. The cells contain 77.2% 95% CD34+ cells, respectively. The specimen was stored in liquid nitrogen and the cells were restored at 37° C. After centrifugation at 1000 rpm/min for 5 min at 4° C., the cells were washed with 0.1 M PBS. Nucleated HUCB were counted using a cytometer to ensure adequate cell number for transplantation. The final dilution is approximately $3 \times 10^6$ HUCB in 500 μl saline for injection in each rat.

2. Animal MCAo Model:

Adult male Wistar rats (n=38) weighing 270–300 g were employed in all experiments. Briefly, rats were initially anesthetized with 3.5% halothane and maintained with 1.0–2.0% halothane in 70% $N_2O$ and 30% $O_2$ using a face mask. Rectal temperature was maintained at 37° C. throughout the surgical procedure using a feedback-regulated water heating system. Transcient MCAo was induced using a method of intraluminal vascular occlusion modified in our laboratory [Chen, et al., *J Cereb Blood Flow Metab* 1992; 12(4): 621–628]. The right common carotid artery, external carotid artery (ECA) and internal carotid artery (ICA) were exposed. A length of 4-0 monofilament nylon suture (18.5–19.5 mm), determined by the animal weight, with its tip rounded by heating near a flame, was advanced from the ECA into the lumen of the ICA until it blocked the origin of the MCA. Two hours after MCAo, animals were reanaesthetized with halothane and reperfusion was performed by withdrawal of the suture until the tip cleared the lumen of the ECA.

3. In vitro-Chemotaxis Assay

1) Ischemia Brain Tissue Extracts:

Animals were sacrificed at 6 h, 24 h and 1 w (n=3 per time point) after the onset of MCAo; a normal control group (n=3) was employed in which the animals were not subjected to surgical procedures. Tissue extracts were obtained from the experimental rats and control rats. Forebrain tissues were immediately obtained from interaural 12 mm to interaural 2 mm [Paxinos et al, The Rat Brain in Stereotaxic Coordinates. Academic Press, San Diego. 1986]. Each specimen was dissected on a bed of ice into hemispheres ipsilateral right side and contralateral to the MCAo. The tissue sections were homogenized by adding IMDM (150 mg tissue/ml IMDM) and incubated on ice 10 min. The homogenate was centrifuged at 100,000 g for 20 min at 4° C. and the supernatant extracted.

2) Ischemia Brain Tissue Extract Assay on HUCB Migration

Chemotactic activity of ischemia brain tissue extracts toward HUCB at different time points was evaluated by using 48-well micro chemotaxis chamber technique, as described [Xu et al, Hematology, 4:345–356, 1999] with some modification. HUCBs were resuspended in IMDM (serum free) at $10^6$ cells/ml. Twenty-five microliters of tissue extracts prepared from normal and ischemic brain at 6 h, 24 h and 1 w after MCAo (150 mg tissue/ml IMDM) were placed in the lower chamber of the 48-well micro chemotaxis chamber. A polycarbonate membrane (8 μm pore size) strip was place over the lower wells and 50μl of HUCB suspension ($1 \times 10^6$ cells/ml) was place in each of the upper wells. Migration of HUCBs was allowed for 5 h at 37° C. incubation and the number of migrated cells into the lower wells was then measured.

4. In Vivo-Treatment with HUCB:

Experimental groups: Group 1 (Control): MCAo alone without donor cell administration (n=10); Group 2: $3 \times 10^6$ human UCB cells injected intravenously at 24 h after MCAo (n=6); The animals of group 1, 2 were sacrificed at 14 days after MCAo. In order to test the effects of delayed (7 day) treatment, we included two additional groups. Group 3 (Control): MCAo alone without donor cell administration (n=5) and rats were sacrificed at 35 days after MCAo; Group 4: $3 \times 10^6$ HUCB cells were injected intravenously at 7 days after MCAo and rats were sacrificed at 35 days after MCAo (n=5).

Implantation procedures: At 1 or 7 days post-ischemia, randomly selected animals received HUCB. Animals were anesthetized with 3.5% halothane and then maintained with 1.0–2.0% halothane in 70% $N_2O$ and 30% $O_2$ using a face mask mounted in a Kopf stereotaxic frame. Approximately, $3 \times 10^6$ HUCB cells in 0.5 ml total fluid volume were injected into a tail vein.

Functional tests: In all animals, a battery of behavioral tests were performed before MCAo, and at 1, 7, 14, 21, 28, 35 days after MCAo by an investigator who was blinded to the experimental groups. The battery of tests consisted of:

1) Rotarod test: An accelerating rotarod was used to measure rat motor function [Hamm R. J., *J Neurotrauma* 11(2): 187–196 1994; and Chen, *J Med;* 31(1–2):21–30, 2000]. The rats were placed on the rotarod cylinder and the time the animals remained on the rotarod was measured. The speed was slowly increased from 4 rpm to 40 rpm within 5 min. A trial ended if the animal fell off the rungs or gripped the device and spun around for two consecutive revolutions without attempting to walk on the rungs. The animals were trained 3 days before MCAo. The mean duration (in seconds) on the device was recorded with 3 rotarod measurements one day before surgery. Motor test data are presented as percentage of mean duration (three trials) on the rotarod compared with the internal baseline control (before surgery).

2) Adhesive-removal somatosensory test [Schallert, Brain Res 379(1): 104–111 1986; Hernandez, Exp Neurol, 102 (3): 318–324 1988; Zhang, *Neurol Sci,* 174(2): 141–146, 2000; and Chen, Neuropharmacology, 39(5): 711–716 2000]. Somatosensory deficit was measured both pre- and postoperatively. All rats were familiarized with the testing environment. In the initial test, two small pieces of adhesive-backed paper dots (of equal size, 113.1 $mm^2$) were used as bilateral tactile stimuli occupying the distal-radial region on the wrist of each forelimb. The rat was then returned to its cage. The time to remove each stimulus from forelimbs was recorded on 5 trials per day. Individual trials were separated by at least 5 min. Before surgery, the animals were trained for 3 days. Once the rats were able to remove the dots within 10 seconds, they were subjected to MCAo.

3) Modified Neurological severity score (mNSS): [Borlongan, *Brain Res;* 676(1): 231–234 1995; Shohami, *Brain Res,* 674(1): 55–62, 1995; Chen, *Neurotrauma.* 1996; 13(10):557–568 1996; Shaller Adv Neurol, 73:229–238, 1997]. Neurological function was graded on a scale of 0 to 18 (normal score 0; maximal deficit score 18). mNSS is a composite of motor, sensory, reflex and balance tests [Germano, *J Neurotrauma;* 11(3):345–353 1994]. In the severity scores of injury, one score point is awarded for the inability to perform the test or for the lack of a tested reflex; thus, the higher score, the more severe is the injury.

5. Histological and Immunohistochemical Assessment:

Animals were allowed to survive for 14 or 35 days after MCAo, and at that time animals were reanaesthetized with ketamine (44 mg/kg) and xylazine (13 mg/kg). Rat brains were fixed by transcardial perfusion with saline, followed by perfusion and immersion in 4% paraformadehyde, and the brain, heart, liver, spleen, lung, kidney and muscle were embedded in paraffin. The cerebral tissues were cut into seven equally spaced (2 mm) coronal blocks. A series of adjacent 6 μm-thick sections were cut from each block in the coronal plane and were stained with hematoxylin and eosin (H&E). The seven brain sections were traced using the Global Lab Image analysis system (Data Translation, Malboro, Mass.). The indirect lesion area, in which the intact area of the ipsilateral hemisphere was subtracted from the area of the contralateral hemisphere, was calculated [Swanson, *J. Cereb Blood Flow Metab*, 10(2): 290–293, 1990]. Lesion volume is presented as a volume percentage of the lesion compared to the contralateral hemisphere.

Single and double immunohistochemical staining [Li, *Brain Res*, 838(1–2): 1–10, 1999] was used to identify cells derived from HUCB. Briefly, a standard paraffin block was obtained from the center of the lesion, corresponding to coronal coordinates for bregma −1~1 mm. A series of 6 µm thick sections at various levels (100 µm interval) were cut from this block and were analyzed using light and fluorescent microscopy (Olympus, BH-2). To detect the distribution of transplanted HUCB cells in other organs (i.e. heart, liver, lung, spleen, kidney and muscle, bone marrow), 3 sections (6 µm thick, 100 µm interval) from each organ were obtained and numbers MAB1281 reactive cells measured. MAB1281 (Mouse Anti-human nuclei monoclonal antibody, Chemicon International, Inc) is markers for human [Vescovi, et al., *Exp Neurol;* 156(1):71–83 1999]. After deparaffinization, sections were placed in boiled citrate buffer (pH 6.0) within a microwave oven (650–720 W). After blocking in normal serum, sections were treated with the monoclonal antibody (mAb) against MAB 1281 diluted at 1:300 in PBS with FITC staining for identification HUCB. Analysis of MAB1281 positive cells is based on the evaluation of an average of 10 histology slides of brain, 3 slides from each organ per experimental animal.

To visualize the cellular co-localization of MAB1281 and cell-type-specific markers in the same cells, fluorescein isothiocyanate conjugated antibody (FITC, Calbiochem, Calif. and red cyanine-5.18) was employed for double-label immunoreactivity. Each coronal section was first treated with the primary MAb1281 mAb with FITC staining for identification HUCB. As described above, and were followed with cell-type-specific antibodies, a neuronal nuclear antigen (NeuN for neurons, dilution 1:200; Chemicon, Calif.), microtubule associated protein 2 (MAP-2 for neurons, dilution 1:200; Boehringer Mannheim) and glial fibrillary acidic protein (GFAP for astrocytes, dilution 1:1000; Dako, Calif.) and FVIII (Von Willebrand Factor, dilution: 1:400; Dako)with CY5 staining. Negative control sections from each animal received identical preparations for immunohistochemical staining, except that primary antibodies were omitted. A total of 500 MAb1281 positive cells per animal were counted to obtain the percentage of MAb1281 cells colocalized with cell type specific markers (MAP-2, NeuN, GFAP, FVIII) by double staining.

Laser Scanning Confocal Microscopy (LSCM): Colocalization of MAB1281 with neuronal (NeuN, MAP-2, GFAP) and endothelial cell (FVIII) markers were conducted by LSCM using a Bio-Rad MRC 1024 (argon and krypton) laser-scanning confocal imaging system mounted onto a Zeiss microscope (Bio-Rad, Cambridge, Mass.) [Zhang ZG, 1999] For immunofuorescence double-labbeled coronal sections, green (FITC for HUCB) and Red cyanine-5.18 (Cy5 for MAP-2, NeuN or GFAP) fluorochromes on the sections were excited by a laser beam at 488 nm and 647 nm; emissions were sequentially acquired with two separate photomultiplier tubes through 522 nm and 680 nm emission filters, respectively. Areas of interest were scanned with a 40× oil immersion objective lens in 260.6×260.6 m format in the x-y direction and 0.5 m in z direction.

6. Statistical Analysis:

The behavior scores (rotarod test, adhesive-removal test and NSS) were evaluated for normality. Repeated measures analysis of variance was conducted to test the treatment by time interactions, and the effect of treatment over time on the behavior score. If an interaction of treatment by time or overall treatment effect were significant at the 0.05 level, the subgroup analysis would be conducted for the effect of treatment at each time point at level 0.05. Otherwise, the subgroup analysis would be considered as exploratory. The means (STD) and p-value for testing the difference between treated and control groups are presented.

To evaluate the chemotactic activity of HUCB migration, counts of intact cells were performed on the normal brain tissue extracts, and ischemic brain tissue extracts at 6 h, 24 h and 1 week of ischemic onset. We tested the normality and equal variances of each outcome measure. Data transformation or permutation tests would be considered, if data were ill behaved. The HUCB migration active were evaluated between normal tissue and ischemic tissues, respectively. The main effect was significant at level 0.05, then subgroup analysis would be considered with a significant effect at level of 0.05. The means (std) are reported.

Results

Figure 3A:
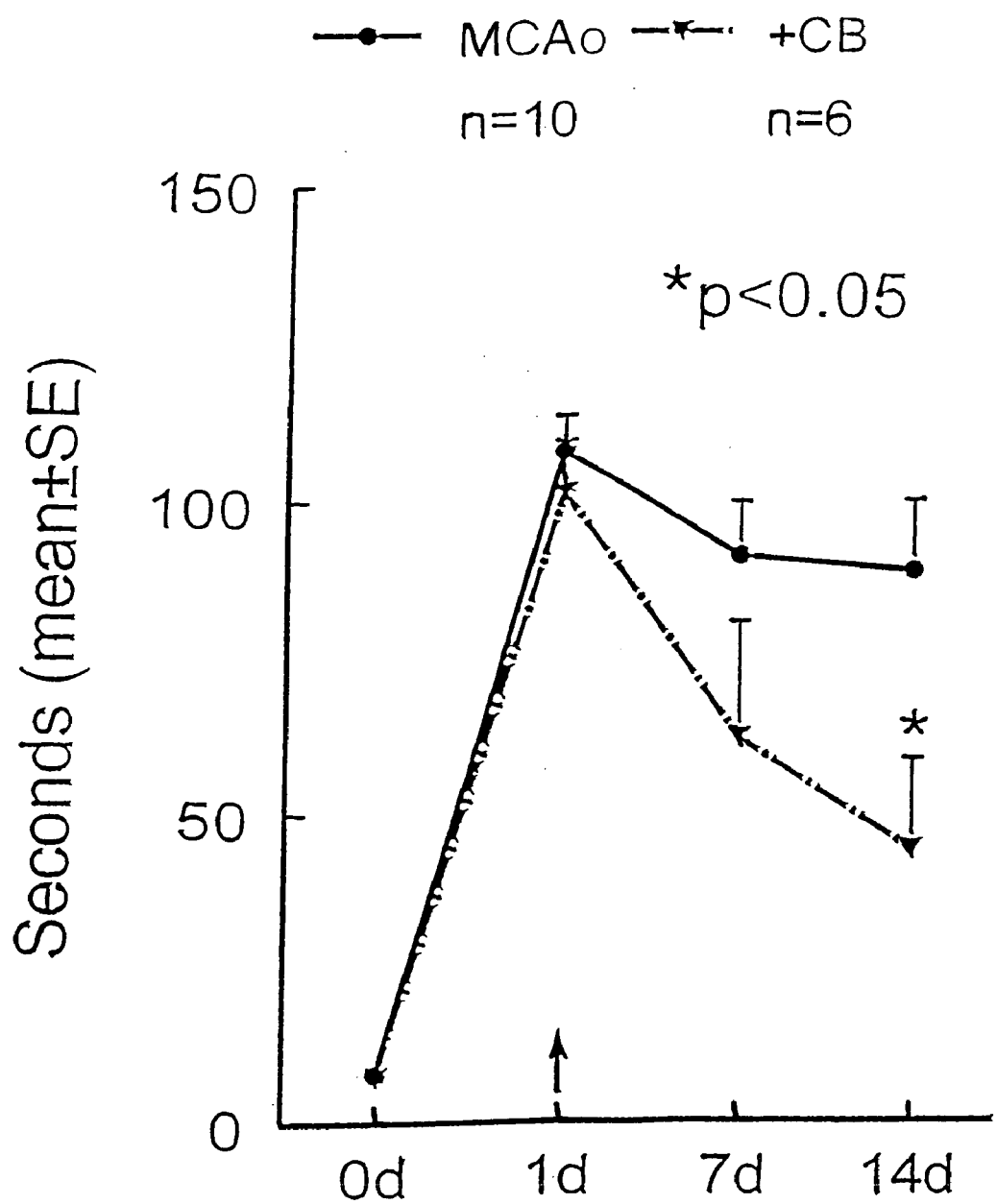
FIGS. 3A, 3B and 3C show the results of neurological function recovery in animals receiving a mononuclear fraction of human umbilical cord blood 1 day after MCAo as evidenced by adhesive removal, rotarod and NSS tests.
Figure 3B:
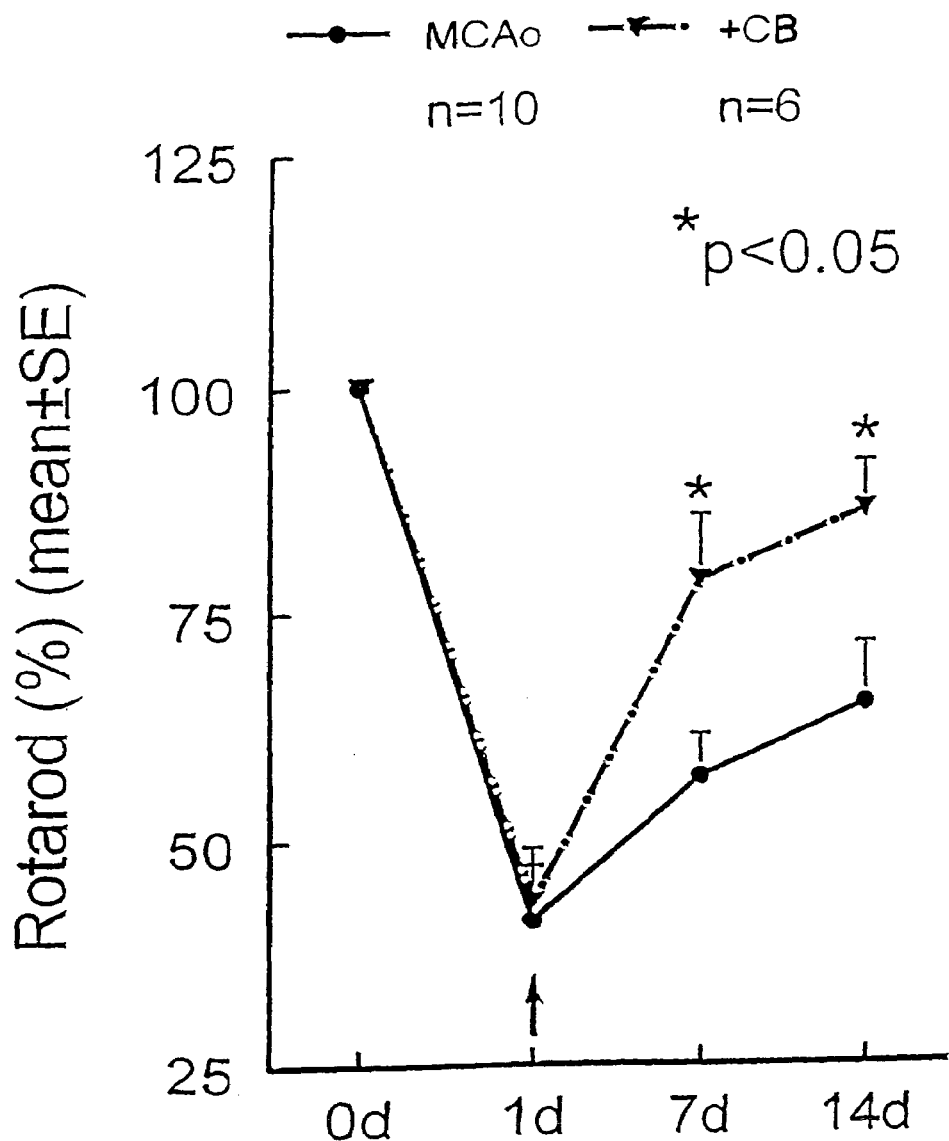
Figure 3C:
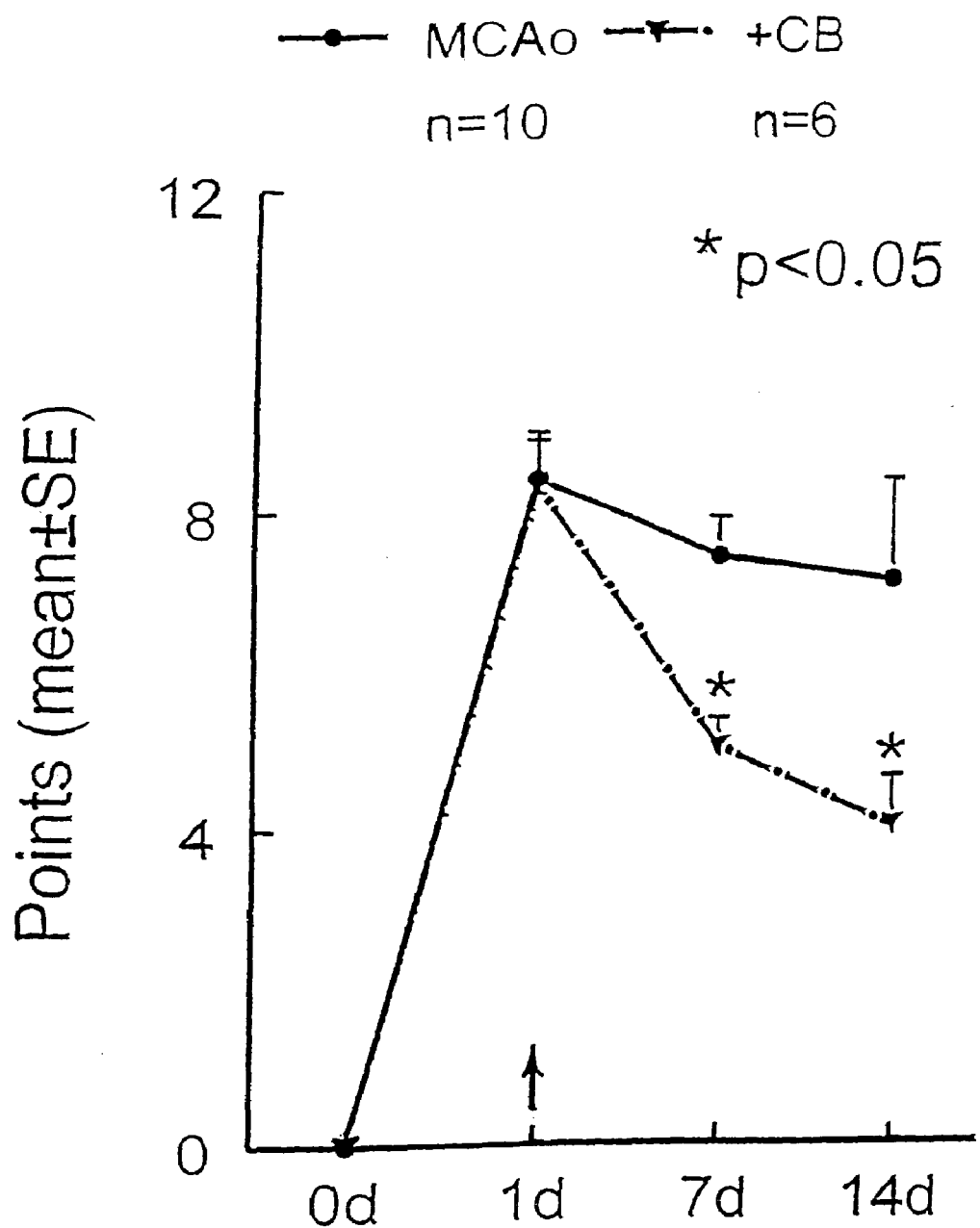
Figure 4A:
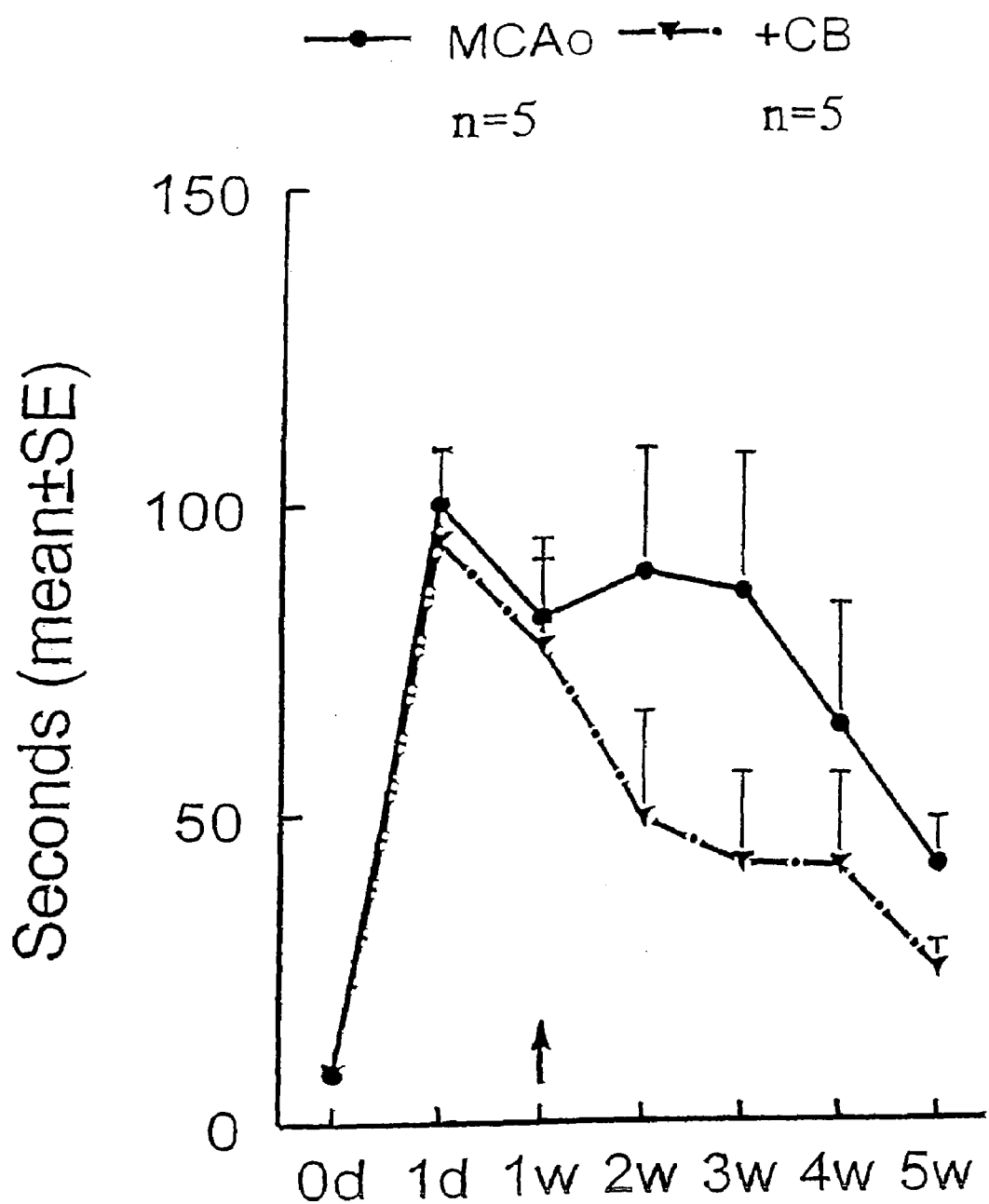
FIGS. 4A, 4B and 4C show the results of neurological function recovery in animals receiving a mononuclear fraction of human umbilical cord blood 7 days after MCAo as evidenced by adhesive removal, rotarod and NSS tests.
Figure 4B:
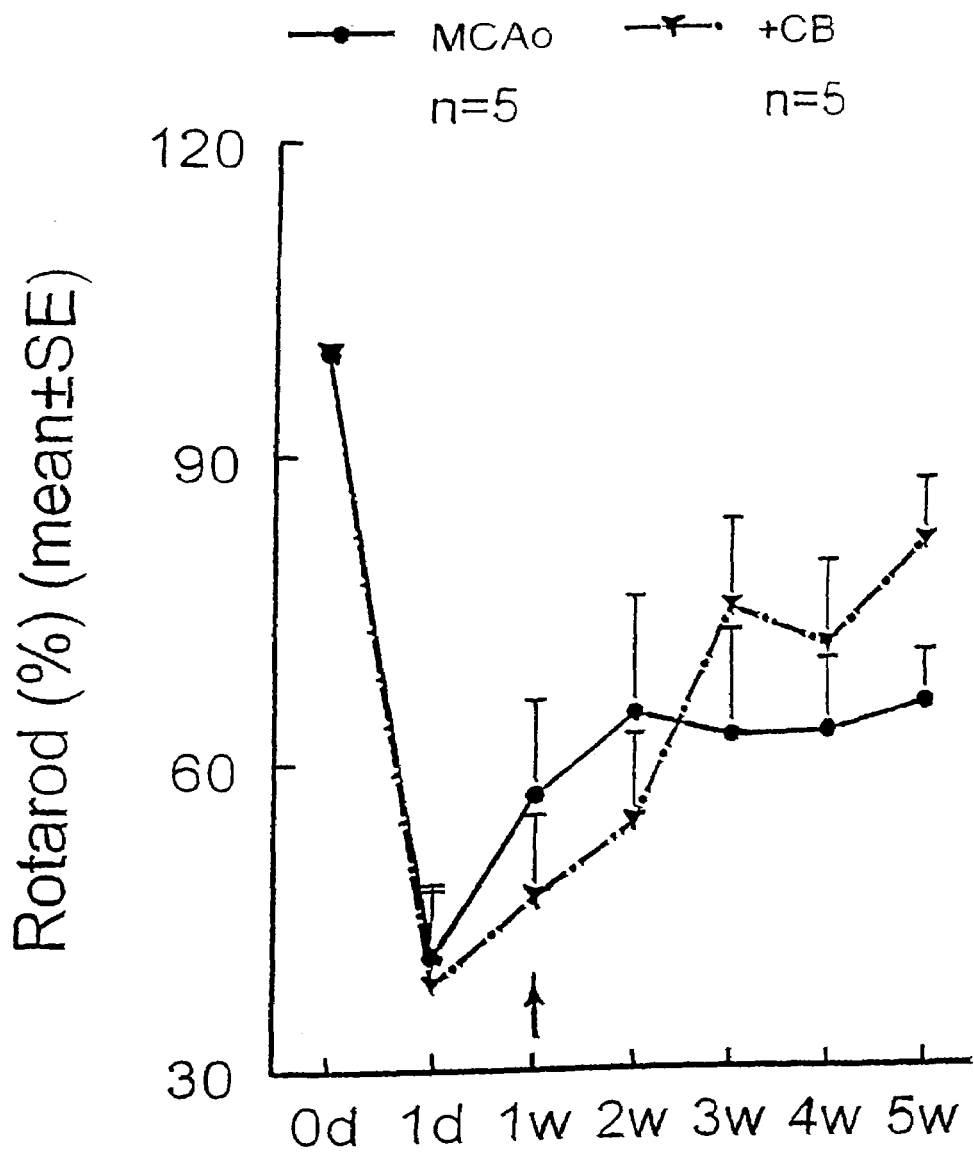
Figure 4C:
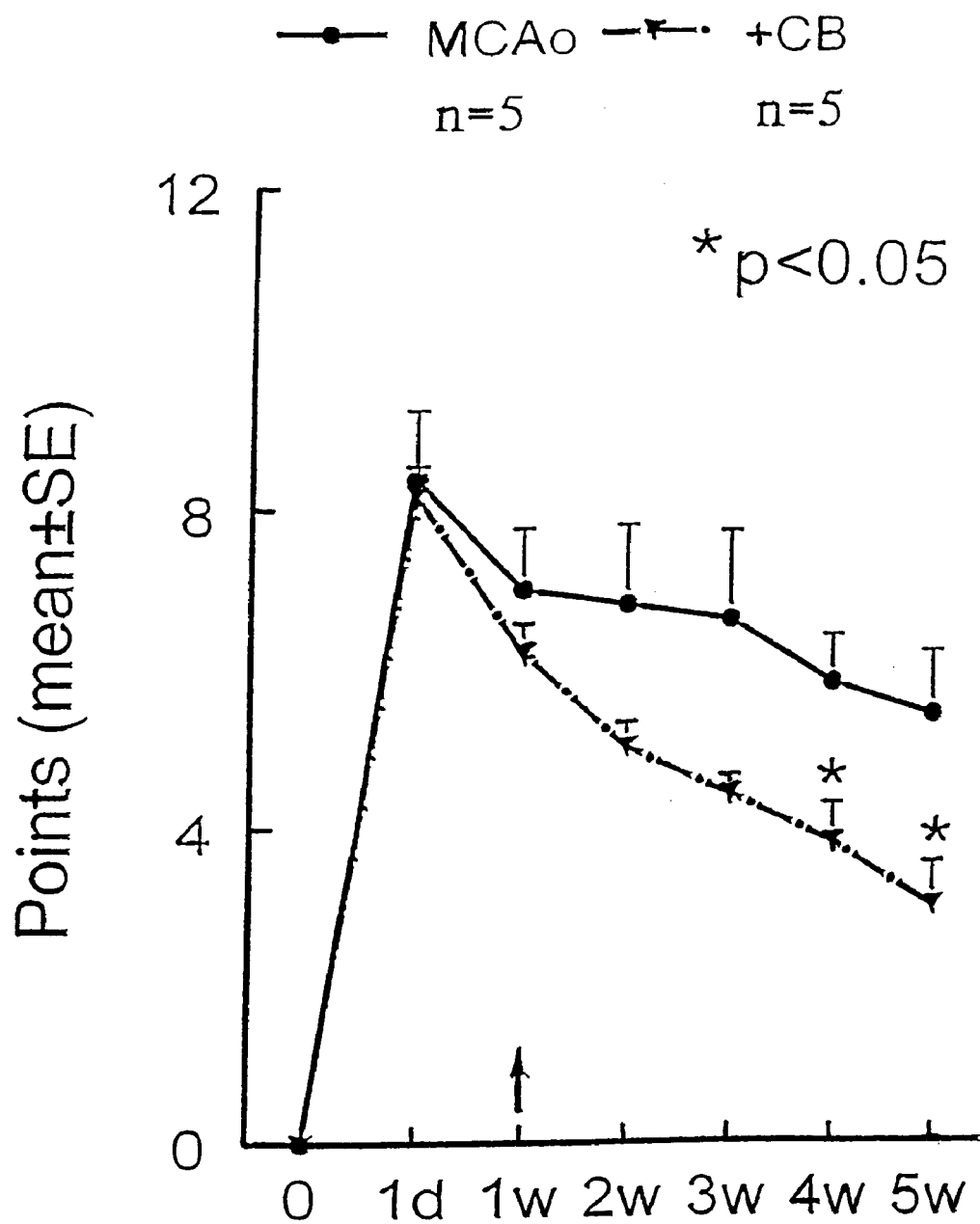

Functional tests: Rats treated with HUCB cells at 24 h after stroke showed no treatment by time interaction for each treatment group on each neurobehavioral score (p-value for interactions >0.13). The overall treatment effect was significant on NSS with $p<0.01$, adhesive-removal test $p=0.04$ and rotarod test $p=0.01$. FIGS. 3A, 3B and 3C shows that treatment at one day after MCAo with HUCB significantly improved functional recovery at 14 days as evidenced by rotarod, adhesive-removal test and NSS scores ($p<0.05$). Rats treated with HUCB at 7 days after stroke showed no treatment by time interaction on neurobehavioral scores with p-value for interaction at 0.88 for NSS, 0.41 for the adhesive-removal test and 0.09 for the rotarod test scores. The overall treatment effect was significant only on NSS with $p<0.05$, and no treatment effect on the other tests ($p=0.15$ for adhesive removal test and 0.55 for rotarod test score) was detected. FIGS. 4A, 4B, 4C show treatment at 7 days after MCAo with HUCB significantly improved functional on NSS test ($p<0.05$) at 28 day and 35 day after MCAo compared to control group. However, rotarod and adhesive-removal tests failed to show a significant difference compared to control animals.

Figure 5:
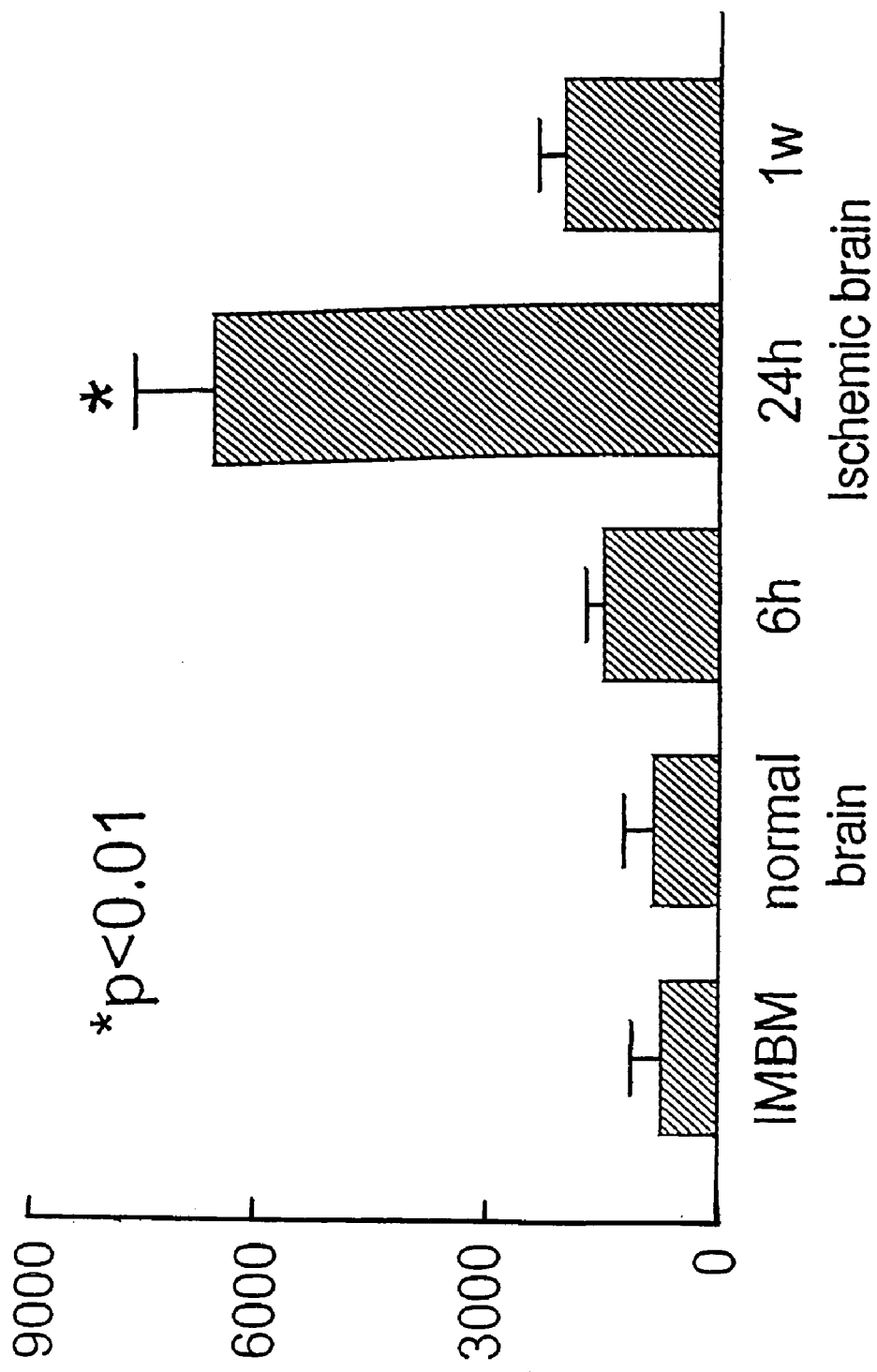
FIG. 5 shows the results of immunostaining of brain sections with MAB1281 and evidences that the highest concentrations of cord blood cells migrate to the injured tissue.

Histology: Within the 6 µm thick coronal sections stained with H&E, dark and red neurons were observed in the ischemic core of all rats subjected to MCAo with and without donor transplantation at 14 and 35 days after MCAo. No significant reduction of volume of ischemic damage was detected in rats with donor treatment at 24 h and 7 days after ischemia, compared with control rats subjected to MCAo alone. Within the brain tissue, identification of HUCB was characterized by MAB1281 staining. HUCB survived and were distributed throughout the damaged brain of recipient rats [FIG. 5]. MAB1281 reactive cells were observed in multiple areas of the ipsilateral hemisphere, including cortices and striatum of the ipsilateral hemisphere. The vast majority of MAB1281 reactive cells were located in the ischemic boundary zone [FIG. 5]. Few cells were observed in the contralateral hemisphere. The data indicate that HUCB cells delivered to brain via an intravenous route preferably migrate into the injured tissue. Some MAB 1281 positive cells encircle vessels, and some cells were detected in the nuclei of the capillary endothelial cells surrounding the injury area [FIG. 5].

Double staining immunohistochemistry of brain sections revealed that some MAB 1281-positive cells were reactive for the astrocyte marker GFAP, neuronal markers NeuN and MAP-2, for endothelial cell marker FVIII. The percentage of MAB1281 labeled expressed GFAP, NeuN, MAP-2 and FVIII proteins was (~6)%, (~3)%, (~2%) and (~8%), respectively.

Ischemia Brain Tissue Extract Assay on HUCB Migration:

HUCB cells migrate in the presence of normal brain tissue and ischemic tissue obtained at 6 h, 24 h and 1 w after MCAo. A significant increase in HUCB migration activity was detected in the presence of ischemic cerebral tissue harvested at 24 h after the onset of stroke (p<0.01). A trend of increase in HUCB migration activity was apparent on tissue harvested at 6 hour and 1 week after MCAo (p>0.09) compared to HUCB migration activity measured in the presence of on normal non-ischemic brain tissue.

Results/Conclusions

The above-described experiments reveal that at 14 days and 35 days after transplantation, intravenously injected HUCB were found in the brain, and significantly more MAB 1281 positive cells were found in the ipsilateral hemisphere than in the contralateral hemisphere. Many cells migrated into the boundary zone of ischemic brain and some cells surrounded vessels. HUCB survive, and some express of cell-type-specific marker GFAP, NeuN and MAP-2. Most important, a significant improvement in functional outcome on motor, sensory and modified NSS tests was found in animals given HUCB intravenously at 1 day after stroke. In vitro, our data showed there was significant HUCB migration activity in the presence of ischemic cerebral tissue harvested at 24 h after MCAo (p<0.01) compared to normal non-ischemic brain tissue. The HUCB treatment at ischemia 24 h promoted more HUCB migration into ischemic brain that may facilitate to functional recovery after MCAo.

In this study, it is shown that intravenous infusion of HUCB enter brain, survive, differentiate and reduce neurological deficits after stroke. In the study, a small percentage of HUCB cells expressed proteins phenotypic of neuronal-like cells. Functional recovery was found within days after administration HUCB.

It was also shown that more HUCB were found in the lesioned hemisphere than in the intact Hemisphere as well as that ischemic brain tissue extracts induced migration of HUCB, suggesting that ischemia induced chemotactic factors facilitate UCB migration.

The results described herein show that HUCB treatment at 24 h after MCAo in the present studies produced significant improved functional recovery (motor rotarod, somatosensory adhesive-removal test and NSS scores) after stroke. Treatment with HUCB at 7 days after MCAo showed functional recovery only on NSS test after MCAo. However, rotarod and somatosensory adhesive-removal test did not shown significant recovery. The treatment benefit of HUCB, thus, may depend on the time of treatment. The treatment benefit may be interrelated to the migration activity of HUCB. A significant increase in HUCB migration activity was detected in the presence of ischemic cerebral tissue harvested at 24 h after MCAo. Treatment with HUCB at ischemic early may promote HUCB migration into ischemic brain and facilitate functional recovery after MCAo.

Almost 25% of cord blood harvests rapidly give rise to a well-established layer of fibroblastoid (MIC) cells. The rapid growth of these cells seems to be sustained by a population of (self-renewing) quiescent (G)) cells. MPC have large ex vivo expansion capacity as well as on their differentiation potential cord blood-derived MPCs can be visualized as attractive targets for cellular or gene transfer therapeutic options.

In conclusion, the experiments presented have shown that intravenously administrated HUCB survive, migrate and improve functional recovery after stroke. Although the mechanism is unclear, the described experiments support the use of umbilical cord blood derived neural cells for the treatment of stroke.

Example

Parenteral Administration of Human Umbilical Cord Blood in Reducing Neurological Deficits After Traumatic Brain Injury Materials and Methods Preparation of Human Umbilical Cord Blood for Injection. The human umbilical cord blood used was a gift from Cryocell International, INC. (Clearwater, Fla.). The specimen was stored in liquid nitrogen and the cells were restored at 37° C. After centrifugation at 1000 rpm/min for 10 min at 4° C., the supernatant was removed and the cells were washed with 0.1 M PBS two times. 30 ul of the cell suspension was mixed with 30 ul of 0.4% trypan blue stain and the number of the viable cells was counted with a hemacytometer and a counter under a phase contrast microscope. The total number of the harvested cells was calculated and the final dilution was $2 \times 10^6$ cells in 300 µl saline.

Controlled Cortical Injury Animal Model and the Injection of HUCB. Wistar rats were anesthetized with 350 mg/kg body weight chloral hydrate, intraperitoneally. Rectal temperature was controlled at 37° C. with a feedback regulated water-heating pad. A controlled cortical impact device was used to induce the injury. Rats were placed in a stereotactic frame. Two 10 unn diameter eraniotomies were performed adjacent to the central suture, midway between lamda and bregma. The second craniotomy allowed for movement of cortical tissue laterally. The dura was kept intact over the cortex. Injury was induced by impacting the left cortex (ipsilateral cortex) with a pneumatic piston containing a 6 mm diameter tip at a rate of 4 m/s and 2.5 mm of compression. Velocity was measured with a linear velocity displacement transducer.

Twenty four rats subjected to TBI were divided into three groups. Experimental group (n=8): 24 hours after TBI, rats were slowly injected over a 10 minute duration with $2 \times 10^6$ cells in 300 gl saline via a tail vein. Placebo control group (n=8): 24 hours after TBI, rats were slowly injected over a 10 minute duration with 300 gl saline via a tail vein. TBI only group (n--8): the rats only were subjected to TBI and no treatment. All rats were killed 28 days after the treatment.

Tissue Preparation. (1) Paraffin sections: Four animals from each group were euthanized with an overdose of ketamine and xylazine administered intraperitoneally and perfused with intra-cardiac heparinized saline followed by 10% buffered formalin. The brains, hearts, lungs, livers, kidneys, spleens, muscle and bone marrow were removed and stored in 10% buffered formalin for 24 hours. Seven standard 2 mm thick blocks were cut on a rodent brain matrix and then embedded with paraffin. Two millimeter thick blocks of the other organs were also cut and embedded with paraffin. A series of adjacent 6 gm thick sections were cut and a section of each block of the brain and other organs was stained with H&E. Standard H&E staining was employed for morphological analysis under light microscopy. (2) Vibratome sections: An additional four rats from each group received the intravenous administration of 1 ml of saline containing fluorescein isothiocyanate (FITC)-dextran (50 mlg/ml, 2×10⁶ molecular weight; Sigma, St. Louis, Mo.). This dye circulated for 1 min, after which the anesthetized rats were killed by decapitation. The brains were rapidly removed from severed heads and placed in 4% paraformaldehyde at 4° C. for 48 hr. Coronal sections (100 [tm) were cut on a vibratome.

Immunohistochemistry. Single staining was performed for identification of HUCB cells using a primary mouse anti-human nuclei monoclonal antibody (MAB1281) and secondary Cy5-conjugated F (ab')2 Fragment rabbit anti-mouse IgG in the coronal sections of all organs. Double staining was also performed on coronal cerebral sections. Brains sections were initially stained for neuronal markers, NeuN and MAP-2, or an astrocytic marker, glial fibrillary acidic protein (GFAP), with the correspondence primary antibodies and the secondary FITC-conjugated F (ab')2 fragment, and subsequently double stained with primary MAB1281 antibody and second antibodies of Cy5-conjugated-F(ab')2 fragment for identification of human umbilical cord blood cells. Briefly, 6 m thick sections from TBI, TBI+saline and TBI+HUCB groups were deparaffinized and the sections were put in boiling citrate buffer (pH=6) in a microwave oven for 10 min for identification of neurons. After cooling at room temperature, the sections were incubated in 0.1% saponin-PBS at 4° C. overnight for mAb NeuN (dilution 1:400, Chemicon) and MAP-2 (dilution 1:400, Chemicon). Antimouse FITC-conjugated F (ab')2 fragment (dilution 1:20, Calbiochem, CA) was then added and incubated for one week. To identify astrocytes, the sections were treated with 0.1% pepsin 37° C. for 15 min and then pAb GFAP (dilution 1:400, Dakopatts) was added. The sections were incubated with antirabbit FITC-conjugated F (ab')2 fragment (dilution 1:20, Calbiochem, CA) for one week. The above sections stained with FITC-conjugated F (ab') fragment were subsequently processed for identification of a human cellular nuclei antigen with a primary mouse anti-human nuclei monoclonal antibody, MAB1281 (dilution, 1:200) and a Cy5-conjugated F (ab')2 fragment rabbit anti-mouse IgG (dilution, 1:20). The slides were analyzed using a fluorescent microscope (Olympus, BH-2). Negative control sections from each animal received identical staining preparation, except that the primary antibodies or the secondary antibodies were omitted.

Three-dimensional image acquisition. In order to observe the relation of the donor's cells with the cerebral vessels, the vibratome sections were analyzed with a Bio-Rad (Cambridge, Mass.) MRC 1024 (argon and krypton) laser-scanning confocal imaging system mounted onto a Zeiss microscope (Bio-Rad). With the FITC-perfused tissue samples from each group, 10 vibratome sections from interaural 6.38 mm to interaural 1.0 nun (Paxions and Watson, 1986) at 2 mm interval were screened at 488 um under a 10× objective lens. Sections stained with the MAB antibody (Cy5) were excited by a laser beam at 647 nm.

Estimates of Cell Number. For measurement of MAB 1281 reactive cells, an average nmber of five equally spaced slides (approximately 100 p.m interval) were obtained from each brain block and MAB 1281 reactive cells were counted within the seven 2 mm thick blocks encompassing the forebrain. Nine slides from each of these blocks were first stained with FITC staining for identification NeuN (3 slides), MAP-2 (3 slides) and GFAP (3 slides), and were followed by Cy5 staining for identification of HUCB cells. The number of the MAB 1281 reactive cells expressing NeuN, MAP-2 and GFAP were counted, respectively, using fluorescent microscopy within all seven blocks. In order to reduce biases introduced by sampling parameters, all sections for MAB 1281 identification from rats were stained simultaneously. The criteria for MAB 1281 positive cells were defined before the cells were counted by observers blinded to the individual treatment. All MAB 1281 reactive cells were counted throughout the coronal sections.

Neurological Functional Evaluation. Neurological motor measurement was performed using an accelerating Rotarod-motor test. The rats were placed on the accelerating Rotarod treadmill (Lab-line instruments, INC) and the rat's task was to walk and maintain its equilibrium on the rotating rod that rotates at a gradually increasing speed. When the rat falls off the rod, a plate trips and a liquid crystal records the endurance time in seconds. All rats were pre-trained with five trials (warm up trials) performed daily for 3 days prior to TBI to ensure stable baselines. After TBI and TBI following administration of HUCB or saline, the rats were tested on days 1, 4, 7, 14 and 28 until sacrifice. The motor test data are shown as a percentage of an average of five trials on the rotarod test compared with the internal baseline values.

Twenty four hours after TBI or administration of HUCB or saline, all rats were evaluated using the neurological severity scores (NSS). NSS is a composite of the motor (muscle status, abnormal movement), sensory (visual, tactile and proprioceptive) and reflex tests. One point was given for failure to perform a task. Thus, the higher score, the more severe is injury, with a maximum of 14 points. Rats were reevaluated on days 1, 4, 7, 14 and 28 after the treatment. All measurements were performed by observers blinded to individual treatment.

Statistical Analysis. NSS and Rotarod tested scores were measured before injury and at 1, 4, 7, 14 and 28 days after TBI. The numbers of MAB 1281 reactive cells were counted at 28 days after treatment. We were primarily interested in the effect of HUCB on the recovery of NSS. The analysis began by testing the difference in means of NSS between the two control groups. If there was no difference between the two controls at 0.05 level, the two control groups were combined to increase the power. The analysis of covariance for ANOVA (repeated measures) was conducted to test the treatment by time interactions, and the effect of treatment over time. If an interaction of time by time was detected at 0.10 level, then the subgroup analysis was conducted for the effect of treatment at each time point at level 0.05. Otherwise, the subgroup analysis was considered as exploratory. The same analysis approach was used to analyze the outcome of Rotarod test score. Paired-t test was used to test the difference in means of cell counts between the injured hemisphere and the control hemisphere.

Results

Histological analysis of organs. Sections from the blocks of brain and organs were stained with H&E staining for the general histopathologieal evaluation. The architectural integrity of all organs analyzed under light microscopy was not disrupted except for the initial mechanical injury of the brain. Bleeding, invasion of white cells, inflammatory response and neoplasm were not observed on any slides aside from brain.

Distribution of MAB 1281 positive cells. No MAB 1281 positive cells were observed in the slides from only TBI and TBI+saline groups which did not receive the injection of HUCB. Large numbers of MAB 1281 positive cells were found in the vessels of the brain, heart, lung, liver, kidney, spleen, muscle and even bone marrow of the rats receiving the injection of HUCB. A few scattered MAB 1281 positive cells were found in the parenchyma of these organs. In brain, MAB 1281 labeled cells were observed in the boundary zone of the injured area, cortex, striamm and corpus callosum of the ipsilateral hemisphere. The MAB 1281 positive signals were detected in the nuclei of the capillary endothelial cells surrounding the injured area. Using laser confocal microscopy, the implanted cells were confirmed to be integrated into sprouting vessels in the boundary zone of the injured area. The total number of MAB 1281 positive cells migrating into the parenchyma of both the ipsilateral and contralateral hemispheres of the brain was counted and analyzed in the TBI+HUCB group. The numbers of MAB 1281 positive cells in the ipsilateral hemisphere (43,597±4265) were significantly greater than those in the contralateral hemisphere (13,742±6471, $p < 0.05$). The data indicate that HUCB cells delivered to brain via an intravenous route preferably migrate into the injured tissue.

Phenotypical Identification of MAB 1281 reactive cells. Double fluorescent staining showed that some MAB 1281 positive cells expressed neuronal markers, NeuN and MAP-2, and an astrocytic marker, GFAP. These double-labeled cells were observed only in the ipsilateral hemispheres of the rats in the HUCB treated group. Most of these positive cells were located in the boundary zone of the injured area. 6.9±1.3% of MAB 1281 labeled cells in the ipsilateral hemispheres in the HUCB treated group expressed NeuN. 5.8±2.4% expressed MAP-2 and 9.7+−2.8% expressed GFAP. These data demonstrate that some implanted cells express neuronal and astrocytic phenotypes.

Neurological and Motor Function Evaluation. Two days after TBI, significantly lower scores of Rotarod test and significantly higher scores of NSS in three groups compared to preinjury were found. Rotarod Test scores were significantly improved in TBI+HUCB group (138.0±11.3% and 155.2±16.2%) when compared with TBI (118.5±17.0% and 129.2±12.2%) and TBI+ saline group (117.2±13.6% and 133.2±10.7% ($p<0.05$) at days 14 and 28 after administration of HUCB. The neurological severity scores were also significantly improved in TBI+HUCB group (4.2±1.3 and 3±0.8) when compared with TBI group (7.5±1.73 and 6.3±1.3) and TBI+saline group (7.3±0.9 and 5.75±0.9) ($p<0.05$) at days 14 and 28 after the injection. The results indicate that intravenous administration of HUCB 24 hours after TBI reduced the motor neurological functional deficits caused by TBI.

Conclusions

The major findings of the above-described experiments were: (1) HUCB cells injected intravenously enter brain by day 28 after HUCB cell administration; (2) intravenous injection ogHUCB reduces motor and neurological deficits by days 14 and 28 after administration; (3) the cells migrating into the parenchyma of the brain express the neuronal markers, NeuN and MAP-2, and the astrocytic marker, GFAP; (4) HUCB cells integrated into the vascular wall within target organ; (5) these cells are also present in other organs and primarily localize to the vessels, without any obvious adverse effects. Our data suggest that intravenous administration of HUCB may be useful in the treatment of TBI.

These data demonstrate that a few injected ceils migrate into the parenchyma of the brain, heart, lung, kidney, liver, spleen, muscle and bone marrow. Because our study was designed to measure the effect of HUCB administered intravenously on traumatic brain injury, the numbers of HUCB cells (MAB 1281 positive cells) present in the cerebral parenchyma were counted and analyzed in the TBI+HUCB group. Significantly more MAB 1281 positive cells were found in the ipsilateral hemisphere than in the contralateral hemisphere. This indicates that the injected cells preferably migrate into the injured hemisphere, especially to the boundary zone of the injured area after TBI and that nearly all of the MAB 1281 positive cells expressing NeuN, MAP-2 and GFAP were located in the ipsilateral hemisphere, demonstrating that the micro-environment of the brain after injury may benefit the induction of the differentiation of HUCB stem cells into the neural cell phenotype.

Two tests (Rotarod test and NSS) were used to measure the neurological behavioral responses to experimental injury in rats. The Rotarod Test is a well-established procedure for testing limb motor coordination and balance aspects of motor performance in rats. The NSS is similar to the Rotarod Test and is an economical, simple and rapid test for assessing mild motor, sensory and reflex deficits after TBI. These two tests are generally used for the evaluation of the effects of the drugs on the behavioral responses after TBI and stroke in animals. Fourteen and twenty eight days after intravenous administration of HUCB, the neurological behavioral deficits were significantly reduced in the rats subjected to TBI in the above-described experiments. These data indicate that intravenous administration of HUCB can effectively improve the neurological outcome in rats after TBI and that intravenous administration of HUCB to patients suffering damage to the brain and/or spinal cord represents a viable therapeutic approach for treating such injuries, including traumatic brain injury.

While the invention has been described hereinabove, care should be taken not to limit the invention in a manner which is unintended and is inconsistent with the invention as set forth in the following claims.

The invention claimed is:

1. A method of producing an isolated, differentiated, mononuclear cell from human umbilical cord blood, comprising:
   a) obtaining a cord blood fraction comprising mononuclear cells from said umbilical cord blood, wherein the mononuclear cells comprise progenitor cells;
   b) growing the mononuclear cells in a serum-free medium comprising EGF and bFGF to produce an enriched fraction of progenitor cells; and
   c) culturing the enriched fraction of progenitor cells in a culture medium containing an effective amount of retinoic acid and nerve growth factor (NGF) for a period sufficient to differentiate the progenitor cells to cells bearing neural progenitor markers.

2. The method of claim 1, wherein the retinoic acid is selected from the group consisting of 9-cis retinoic acid, all transretinoic acid and a mixture thereof.

* * * * *